US007045353B2

(12) United States Patent
Benvenisty

(10) Patent No.: US 7,045,353 B2
(45) Date of Patent: May 16, 2006

(54) DIRECTED DIFFERENTIATION OF HUMAN EMBRYONIC CELLS

(75) Inventor: Nissim Benvenisty, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/918,702

(22) Filed: Jul. 31, 2001

(65) Prior Publication Data

US 2002/0146678 A1 Oct. 10, 2002

Related U.S. Application Data

(60) Provisional application No. 60/267,559, filed on Feb. 9, 2001, provisional application No. 60/222,160, filed on Aug. 1, 2000.

(51) Int. Cl.
*C12N 5/02* (2006.01)
*C12N 5/08* (2006.01)

(52) U.S. Cl. .................. 435/377; 435/366; 435/383; 435/384

(58) Field of Classification Search ............... 435/366, 435/377, 396, 397, 405, 406, 325, 368, 372, 435/373, 378, 381, 383, 384
See application file for complete search history.

(56) References Cited

U.S. PATENT DOCUMENTS

| | | | |
|---|---|---|---|
| 5,453,357 A | 9/1995 | Hogan | 435/7.21 |
| 5,459,069 A | 10/1995 | Palsson et al. | 435/289.1 |
| 5,736,396 A | 4/1998 | Bruder et al. | |
| 5,753,506 A | 5/1998 | Johe | |
| 5,843,780 A | 12/1998 | Thomson | 435/363 |
| 5,874,301 A | 2/1999 | Keller et al. | 435/325 |
| 5,914,268 A | 6/1999 | Keller et al. | 435/325 |
| 6,090,622 A | 7/2000 | Gearhart et al. | 435/366 |
| 6,114,168 A | 9/2000 | Samarut et al. | 435/405 |
| 6,197,585 B1 | 3/2001 | Stringer | 435/368 |
| 6,602,711 B1 | 8/2003 | Thomson et al. | 435/378 |

FOREIGN PATENT DOCUMENTS

| | | |
|---|---|---|
| EP | 0 753 574 | 1/1997 |
| EP | 1 016 413 | 7/2000 |
| WO | WO 91/04274 | 4/1991 |
| WO | WO 96/15259 A2 | 5/1996 |
| WO | WO 96/15259 A3 | 5/1996 |
| WO | WO 96/17627 | 6/1996 |
| WO | WO 98/30679 | 7/1998 |
| WO | WO 98/43679 | 8/1998 |
| WO | WO 99/20740 | 4/1999 |
| WO | WO 99/38008 | 7/1999 |
| WO | WO 00/12683 | 3/2000 |
| WO | WO 0017326 | 3/2000 |
| WO | WO 00/70021 | 11/2000 |
| WO | WO 01/05944 | 1/2001 |

OTHER PUBLICATIONS

Thomson et al. Embryonic Stem Cell Lines Derived from Human Blastocyts. Science. Nov. 6, 1998, vol. 282, pp. 1145-1147.*
Keller. In Vitro Differentiation of Embryonic Stem Cells. Current Opinion in Cell Biology. 1995, vol. 7, pp. 862-869.*
Wobus et al. Effects of Growth Factors on Differentiation Capacity of Embryonic Stem Cells In Vitro. Cell Different., vol. 20 (Suppl.) 81S.*
Drab et al. From Totipotent Embryonic Stem Cells to Spontaneously Contracting Smooth Muscle Cells: A Retenoic Acid and db-cAMP In Vitro Differentiation Model. FASEB. 1997, vol. 11, pp. 905-915.*
Vittet et al. Embryonic Stem Cells Differentiate In Vitro to Endothelial Cells Through Successive Maturation Steps. Blood. Nov. 1, 1996, vol. 88, pp. 3424-3431.*
Thomson et al. Embryonic Stem Cell Lines Derived from Human Blastocysts. Science. vol. 282, Nov. 6, 1998, pp. 1145-1147.*
Shamblott et al. Derivation of Pluripotent Stem Cells from Cultured Human Primordial Germ Cells. Proc. Natl. Acad. Sci. (USA). vol. 95, Nov. 1998, pp. 13726-13731.*
Bain et al. Embryonic Stem Cells Express Neuronal Properties In Vitro. Developmental Bio. vol. 168, 1995, pp. 342-357.*
Yuen et al. Generation of a Primative Erythroid Cell Line and Promotion of its Growth by Basic Fibroblast Growth Factor. Blood. vol. 91, May 1, 1998, pp. 3202-3209.*
Wobus et al. Specific Effects of Nerve Growth Factor on the Differentiation Pattern of Mouse Embryonic Stem Cells In Vitro. Biomed. Biochim. Acta. vol. 47, 1988, pp. 965-973.*
Effects of eight growth factors on the differentiation of cells derived from human embryonic stem cells, PNAS, XP-002198709, vol. 97, No. 21, pp. 11307-11312, Oct. 10, 2000.
Maintenance of pluripotential embryonic stem cells by stem cell selection, Reprod. Fertil. Devl. 1998, 10, 527-533P-001070570.

(Continued)

*Primary Examiner*—Deborah Crouch
(74) *Attorney, Agent, or Firm*—Browdy and Neimark, PLLC

(57) ABSTRACT

Methods are described for mapping a pathway of differentiation of a population of embryonic cells which includes exposing the cells to an exogenous factor and measuring gene expression products that are characteristic of a particular cell type or lineage. Directing differentiation of human embryonic cells relies on dissociated embryoid bodies which are then exposed to one or more exogenous factors to enrich a culture for a particular cell type. The differentiated cells may be used for treating a medical condition in a human. Kits for determining differentiation pathways and screening exogenous factors for their utility in differentiation are provided.

6 Claims, 12 Drawing Sheets

OTHER PUBLICATIONS

Retinoic Acid Accelerates Embryonic Stem Cell-Derived Cardiac Differentiation and Enhances Development of Centricular Cardiomyocytes, 1997 Academic Press Limited, J. Mol Cell Cardiol 29, 1525-1539 (1997), XP-002198708.

Single factors direct the differentiation of stem cells from the fetal and adult cental nervous system, Johe, Karl K., et al., Genes & Development, 10:3129-3140, 1996 by Cold Spring Harbor Laboratory Press ISSN 0890-9369/96, XP000867356.

Genetically Selected Cardiomyocytes from Differentiating Embryonic Stem Cells Form Stable Intracardiac Grafts, The American Society for Clinical Investigation, Inc. 0021-9738/96/07/216/09 vol. 98, No. 1, Jul. 1996, 216-224, XP000670716.

Expression of Transforming Growth Factor B2 during the Differentiation of Murine Embryonal Carcinoma and Embryonic Stem Cells, Academic Press, Inc., Developmental Biology 137, 161-170 (1990), XP-000891381.

Elsea et al. The Mousetrap:What We Can Learn When the Mouse Model Does Not Mimic the Human Disease, ILAR Journal, vol. 43, No. 2, pp. 66-79 (2002).

Thomson et al. Primate Embryonic Stem Cells, Curr. Top. in Dev. Biol., vol. 38, pp. 133-165 (1998).

Reubinoff, et al. "Embryonic stem cell lines from human blastocysts: somatic differentiation in vitro," Nature Biotechnology, vol. 18, No. 4, pp. 399-404, (2000).

Jung, et al. "Initiation of Mammalian liver Development from Endoderm by Fibroblast Growth Factors," Science, vol. 284, pp. 1998-2003, (1999).

Itskovitz-Eldor, et al. "Differentiation of Human Embryonic Stem Cells into Embryoid Bodies Comprising the Three Embryonic Germ Layers," Molecular Medicine, vol. 6, No. 2, pp. 88-95, (2000).

Thomson, et al. "Embryonic Stem Cell Lines Derived from Human Blastocysts," Science, vol. 282, pp. 1145-1147, (1998).

* cited by examiner

| Gene | Expected Product | 5' Primer | 3' Primer |
|---|---|---|---|
| α-feto protein (αFP) | 680bp | AGAACCTGTCACAAGCTGTG | CTGAGGATGTC |
| α1 anti-trypsin (α1AT) | 360bp | AGACCCTTGAAGTCAAGGACACCG | CCATTGCTGAAGACCTTAGTGATGC |
| Activin Receptor type IIB (ACTRIIB) | 550bp | ACACGGGAGTGCATCTACTACAACG | TTCATGAGCTGGGCCTTCCAGACAC |
| Albumin | 450bp | CCTTTGGCACAATGAAGTGGGTAACC | andCAGCAGTCAGCCATTCACCATAGG |
| Amylase | 490bp | GCTGGGCTCAGTATTCCCCAAATAC | GACGACAATCTCTGACCTGAGTAGC |
| B-Actin | 400bp | TGGCACCACACCTTCTACAATGAGC | GCACAGCTTCTCTTAATGTCACGC |
| β-Globin (β-Glob) | 410bp | ACCTGACTCCTGAGGAGAAGTCTGC | TAGCCACACACCAGCCACCACTTCTG |
| Bone Morphogenic Protein 4 Receptor type II (BMP4RII) | 800bp | TCTGCAGCTAGGTCCTCTCATCAGC | TATACTGCTCCATATCGACCTCGGC |
| Cardiac Actin (cACT) | 630bp | TCTATGAGGGCTACGCTTTG | CCTGACTGGAAGGTAGATGG |
| Cartilage Matrix Protein (OMP) | 620bp | ATGACTGTGAGCAGGTGTGCATCAG | CTGGTTGATGGTCTTGAAGTCAGCC |
| δ-Globin (δ-Glob) | 430bp | ACCATGGTGCATCTGACTCCTGAGG | ACTTGTGAGCCAAGGCATTAGCCAC |
| Dopamine β Hydroxylase (DβH) | 440bp | CACGTACTGGTGCTACATTAAGGAGC | AATGGCCATCACTGGCGTGTACACC |
| Enolase | 490bp | TGACTTCAAGTCGCCTGATGATCCC | TGCGTCCAGCAAAGATTGCCTTGTC |
| Epidermal Growth Factor Receptor type (EGFR) | 300bp | CAGTCGTCAGCCTGAACATAACATCC | AGGTTGCACTTGTCCACGCATTCCC |
| Fibroblast Growth Factor Receptor type I (FGFRI) | 410bp | AGCATCATAATGGACTCTGTGGTGCC | AGTCCGATAGAGTTACCGCCAAGC |
| Follicular Stimulating Hormone (FSH) | 320bp | GTGAGCTGACCAACATCACCATTGC | TTTCACCAAAGGAGCAGTAGCTGGG |
| Glucagon | 370bp | CTCAGTGATCCTGATCAGATGAACG | AGTCCCTGGCGGCCAAGATTATCAAG |
| Glyceraldehyde 3-phosphate dehydrogenase (G3PD) | 890bp | TGAAGGTCGGAGTCAACGGATTTGGT | CATGTGGGCCATGAGGTCCACCAC |
| Hepatocyte Growth Factor Receptor (c-Met) | 440bp | AGAAATTCATCAGGCTGTGAAGCGCG | TTCCTCCGATCGCACACATTTGTCG |

| FIG. 5A | FIG. 5C |
|---|---|
| FIG. 5B | FIG. 5D |

| | | |
|---|---|---|
| Insulin | 420bp | CTGCATCAGAAGAGGCCATCAAGC | GGCTTTATTCCATCTCTCTCGGTGC |
| Kalikrein | 480bp | GTTCATGTCAGTGAGAGCTTCCCAC | TCACATAAGACAGCACTCTGACGGC |
| Keratin | 780bp | AGGAAATCATCTCAGGAGGAAGGGC | AAAGCACAGATCTTCGGGAGCTACC |
| Lipase | 400bp | GATTCATCAAGCATCAGTGGCTCC | CCAATCGGACTAATTCAGGTGTGCC |
| Myosin light polypeptide2 (myosin) | 400bp | TCCAACGTGTTCTCCATGTTCGAAC | CTTGTAGTCCAAGTTGCCAGTCACG |
| Nerve Growth Factor Receptor (NGFR) | 410bp | TGTTCCTGCCAGGACAAGCAGAAC | TCTTGAAGGCTATGTAGGCCACAAGG |
| Neurofilament Heavy Chain (NFH) | 400bp | TGAACACAGACGCTATGCGCTCAG | CACCTTTATGTGAGTGGACACAGAG |
| Octamer Binding Protein 4 (Oct4) | 140bp | CGPGAAGCTGGAGAAGGAGAAGCTG | CAAGGGCCGCAGCTTACACATGTTC |
| Parathyroid Hormone (PTH) | 290bp | GGCTAAAGTTATGATTGTCATGTTGGC | TCAGCTTTGTCTGCCTCTCCAAGAC |
| PDX-1 | 230bp | GGATGAAGTCTACCAAAGCTCACGC | CCAGATCTTGATGTGTCTCTCGGCT |
| Phosphoprotein enriched in astrocytes(PEA-15) | 820bp | AGAGTGAGGAGATCACTACTGGCAG | ACCTGCTGGTACTCAGGAAACAGTC |
| Renin | 590bp | AGTCGTCTTTGACACTGGTTCGTCC | GGTAGAACCTGAGATGTAGGATGC |
| Retinoic Acid Receptor type alpha (RAR) | 500bp | AGCAGCAGTTCTGAAGAGATAGTGCC | GTGGAGAGTTCACTGAACTTGTCCC |
| Surfactant | 460bp | TCCAGCTCATCTAGATGAGGAGCTC | GTCCCATGGCCTAAATGCCTCTCAG |
| Transforming Growth Factor Receptor type II (TGFRII) | 530bp | TAGTCACTGACAACAACGGTGCAGTC | ACAGTGCTCGCTGAACTCCATGAGC |
| WT1 | 450bp | TCCTTCATCAAACAGGAGCCGAGC | CTGTAGGGCGTCCTCAGCAGCAAAG |

FIG. 5B

| Gene | 5' Primer | 3' Primer |
| --- | --- | --- |
| α-feto protein (αFP) | SEQ ID NO: 4 | SEQ ID NO: 5 |
| α1 anti-trypsin (α1AT) | SEQ ID NO: 6 | SEQ ID NO: 7 |
| Activin Receptor type IIB (ACTRIIB) | SEQ ID NO: 8 | SEQ ID NO: 9 |
| Albumin | SEQ ID NO: 10 | SEQ ID NO: 11 |
| Amylase | SEQ ID NO: 12 | SEQ ID NO: 13 |
| B-Actin | SEQ ID NO: 14 | SEQ ID NO: 15 |
| β-Globin (β–Glob) | SEQ ID NO: 16 | SEQ ID NO: 17 |
| Bone Morphogenic Protein 4 Receptor type II (BMP4RII) | SEQ ID NO: 18 | SEQ ID NO: 19 |
| Cardiac Actin (cACT) | SEQ ID NO: 20 | SEQ ID NO: 21 |
| Cartilage Matrix Protein (OMP) | SEQ ID NO: 22 | SEQ ID NO: 23 |
| δ-Globin (δ–Glob) | SEQ ID NO: 24 | SEQ ID NO: 25 |
| Dopamine β Hydroxylase (DβH) | SEQ ID NO: 26 | SEQ ID NO: 27 |
| Enolase | SEQ ID NO: 28 | SEQ ID NO: 29 |
| Epidermal Growth Factor Receptor type (EGFR) | SEQ ID NO: 30 | SEQ ID NO: 31 |
| Fibroblast Growth Factor Receptor type I (FGFRI) | SEQ ID NO: 32 | SEQ ID NO: 33 |
| Follicular Stimulating Hormone (FSH) | SEQ ID NO: 34 | SEQ ID NO: 35 |
| Glucagon | SEQ ID NO: 36 | SEQ ID NO: 37 |
| Glyceraldehyde 3-phosphate dehydrogenase (G3PD) | SEQ ID NO: 38 | SEQ ID NO: 39 |
| Hepatocyte Growth Factor Receptor (c-Met) | SEQ ID NO: 40 | SEQ ID NO: 41 |

| | | |
|---|---|---|
| Insulin | SEQ ID NO: 42 | SEQ ID NO: 43 |
| Kalikrein | SEQ ID NO: 44 | SEQ ID NO: 45 |
| Keratin | SEQ ID NO: 46 | SEQ ID NO: 47 |
| Lipase | SEQ ID NO: 48 | SEQ ID NO: 49 |
| Myosin light polypeptide2 (myosin) | SEQ ID NO: 50 | SEQ ID NO: 51 |
| Nerve Growth Factor Receptor (NGFR) | SEQ ID NO: 52 | SEQ ID NO: 53 |
| Neurofilament Heavy Chain (NFH) | SEQ ID NO: 54 | SEQ ID NO: 55 |
| Octamer Binding Protein 4 (Oct4) | SEQ ID NO: 56 | SEQ ID NO: 57 |
| Parathyroid Hormone (PTH) | SEQ ID NO: 58 | SEQ ID NO: 59 |
| PDX-1 | SEQ ID NO: 60 | SEQ ID NO: 61 |
| Phosphoprotein enriched in astrocytes(PEA-15) | SEQ ID NO: 62 | SEQ ID NO: 63 |
| Renin | SEQ ID NO: 64 | SEQ ID NO: 65 |
| Retinoic Acid Receptor type alpha (RAR) | SEQ ID NO: 66 | SEQ ID NO: 67 |
| Surfactant | SEQ ID NO: 68 | SEQ ID NO: 69 |
| Transforming Growth Factor Receptor type II (TGFRII) | SEQ ID NO: 70 | SEQ ID NO: 71 |
| WT1 | SEQ ID NO: 72 | SEQ ID NO: 73 |

DIRECTED DIFFERENTIATION OF HUMAN EMBRYONIC CELLS

CROSS REFERENCE TO RELATED APPLICATIONS

This application gains priority from provisional application 60/222,160 filed Aug. 1, 2000 and provisional application 60/267,559 filed Feb. 9, 2001 both applications being incorporated by reference herein.

TECHNICAL FIELD AND BACKGROUND ART

The present invention relates to methods and kits for directed differentiation of embryonic stem cells and their use in vivo and in vitro.

Embryonic stem (ES) cells have been described in the prior art as undifferentiated pluripotent cells derived from the inner cell mass of blastocyst stage embryos which can grow indefinitely in culture while retaining a normal karyotype. Blastocyst derived stem cells form teratomas when injected into muscles or testis of severe combined immunodeficiency mice. Murine embryonic stem cells have been reported to form aggregates or embryoid bodies in vitro which are capable of spontaneously differentiating into various cell types. In contrast to blastocyst derived stem cells, embryoid body derived cells do not appear to form teratomas when implanted in vivo. (Robertson, (1987) *IRL Press, Oxford*, pp. 71–112; Thomson et al. (1998) *Science* Vol 282, pp. 1145–1147; Reubinoff et al. (2000) *Nat. Biotechnol.* Vol 18, pp. 399–404).

While human embryonic stem cells have been recovered from human embryos produced by in vitro fertilization, the formation of embryoid bodies from non-human primates and from humans has been problematic. In contrast to mice, the formation of embryoid bodies from primates, more particularly, the common marmoset (Thomson, (1996) *Biology of Reproduction*, Vol. 55, pp. 254–259, U.S. Pat. No. 5,843,780) and the rhesus monkey (Thomson, (1995) *Proc. Natl. Acad. Sci, USA*, Vol. 92, pp. 7844–7848) were found to be inconsistent and asynchronous. Moreover, differentiation of rhesus embryonic stem cells was disorganized and vesicular structures did not form. In addition, human embryonic stem cells have been shown to differentiate in a spontaneous and uncontrolled manner, so that the experimenter cannot determine which cell types will form in vivo or in vitro (Thomson, et al., (1998) *Science*, Vol. 282, pp. 1145–1147; Reubinoff, et al., (2000) *Nat. Biotechnol*, Vol. 19, pp. 399–404; Itskovitz-Eldor et al., (2000) *Mol. Med.*, Vol. 6, pp. 88–95).

Development of techniques for manipulating differentiation of human embryonic stem cells to provide a uniform population of precursors and differentiated cells of a desired lineage are desirable for in vivo medical uses and for in vitro assays.

Although many useful lessons may be learned about development in mammals from studying mice, not all of development is the same in all animals. Consequently, it is desirable to have tools to analyze and compare pathways in different mammals and to combine these tools with a methodology that permits the isolation, preservation and cultivation of embryonic stem cells from mammals including humans for correcting a disease condition resulting from cell degeneration.

In particular, human embryonic stem cells may be uniquely useful as a source of cells for transplantation in numerous human pathologies, and as a component in biomedical engineering as well as providing clues on early stages of human development.

SUMMARY OF THE INVENTION

In a first embodiment of the invention there is provided a method of mapping a pathway of differentiation of a population of embryonic cells, that includes: (i) selecting: (a) a set of gene expression products, wherein each gene expression product in the set is characteristic of a cell type that has undergone differentiation, such that a plurality of differentiated cell types are represented in the set; and (b) an exogenous factor from a library of exogenous factors; (ii) applying the exogenous factor to a population of cells; (iii) characterizing the effect of the exogenous factor on the differentiation pathway of the undifferentiated cells by determining gene expression products in the set; and (iv) mapping the pathway of differentiation.

According to the above, the gene expression products may include at least one gene expression product that is expressed in the mesoderm, ectoderm and/or endoderm, where the expression product expressed in the ectoderm may be for example, neurofilament heavy chain (NF-H), keratin or adrenal dopamine β hydroxylase (DβH), the expression product expressed in the mesoderm may include any of enolase, renin, cartilage matrix protein (CMP), kallikrein, Wilms Tumor 1 (WT1), cardiac actin (cACT), δ-globin or β-globin, the gene expression product expressed in the endoderm may include albumin, α1-antitrypsin (α1AT), amylase, pancreatic and duodenal homeobox gene 1 (PDX-1), insulin and α-fetoprotein (αFP).

According to the above, examples of exogenous factor include interleukins, basic fibroblast growth factor (bFGF), transforming growth factor (TGFβ1), activin-A, bone morphogenic protein-4 (BMP-4), hepatocyte growth factor (HGF), epidermal growth factor (EGF), β nerve growth factor (NGF) and retinoic acid (RA).

In another embodiment of the invention, a method is provided for directing differentiation of human embryonic cells to a specific cell type, including the steps of (a) permitting a population of embryonic stem cells to form embryoid bodies; (b) dissociating the embryoid bodies to provide embryonic cells for differentiating in the presence of at least one exogenous factor for an effective period of time; and (c) causing directed differentiation of human embryonic cells to form the specific cell type.

According to the above method, the embryoid bodies may be formed in a suspension culture. The embryonic cells may form a monolayer on a substrate. The exogenous factor may be a growth factor, for example an interleukin, nerve growth factor, or retinoic acid. The differentiated cells may be a neuronal cell type and further may have neuronal processes. In all the present embodiments, the embryonic cells may be human.

In another embodiment of the invention, a method is provided of treating a subject suffering from a condition associated with degeneration of cells or malfunction of cells, that includes: (a) accessing dissociated embryoid cells; (b) treating the cells with an exogenous factor; (c) causing the cells to differentiate; and (d) placing an effective amount of differentiated cells into the subject to treat the condition.

According to the above, the condition may be a heart condition in which heart muscle is degenerated. The cells may be treated with an exogenous factor selected from the group consisting of TGF-β, FGF, RA, HGF and EGF and an effective amount of differentiated cells targeted to the heart.

The condition may be a kidney condition in which kidney tissue is degenerated, the cells being treated with NGF and an effective amount of differentiated cells targeted to the kidney. The condition may be a skin condition in which skin tissue is degenerated, the cells treated with BMP-4 and an effective amount of differentiated cells targeted to skin. The condition may be a liver condition in which the liver is degenerated, the cells treated with NGF and an effective amount of differentiated cells targeted to the liver. The condition may be a brain condition in which brain tissue is degenerated, the cells treated with at least one of NGF or RA and an effective amount of differentiated cells targeted to the brain. The condition may be a spinal cord injury in which the neurons are degenerated, the cells treated with at least one of NGF or RA and an effective amount of differentiated cells are targeted to the liver. The condition may be anemia or immunodeficiency and the cells treated with at least one of NGF or interleukin and the differentiated cells targeted to the blood. The condition may be an adrenal condition in which the adrenal tissue is degenerated, the cells treated with RA and an effective amount of differentiated cells targeted to the adrenal tissue.

According to the above, the subject may be a mammal including a human subject. The differentiated cell type may be any of brain cells, liver cells, pancreatic cells, muscle cells, chondrocytes, kidney cells, Mullerian duct cells, heart cells, blood cells, skin cells and adrenal cells.

In another embodiment of the invention, a kit for determining differentiation pathways, is provided that includes: a plurality of sets of cell specific markers forming a panel in an assay format, the assay format including reagents for detecting the cell specific markers, the cell specific markers including a first set of markers that are characteristic of each of the ectoderm, mesoderm and endoderm of the embryo, and a second set of markers that are characteristic of a body tissue, the second set containing more than one marker, and means for detecting reagents bound to cell specific markers.

In another embodiment of the invention, a method for screening an exogenous factor is provided to determine whether the factor is capable of causing directed differentiation in a population of human embryonic cells, including (a) subjecting the population of human embryonic cells to the exogenous growth factor; (b) measuring the expression of receptors, the receptors being of a type that characterizes a particular differentiated cell population; and (c) determining whether the exogenous factor enhances differentiation, maintains differentiation at a normal level or depresses differentiation of the particular cell population.

In another embodiment of the invention, a panel of cell type differentiation determining markers is provided that includes a set of reagents for specifically detecting gene expression of a plurality of ectodermal specific proteins, a plurality of mesodermal specific proteins and a plurality of endodermal specific proteins.

According to the above, the ectodermal specific proteins may include neurofilament protein, keratin and adrenal dopamine β hydroxylase, the mesodermal specific proteins may include enolase, CMP, renin, kallikrein, WTI, cACT, β globin, δ globin and cActin and the endodermal specific proteins may include amylase, α-FP, PDX-1 and insulin. The reagents may include DNA primers or antibodies.

BRIEF DESCRIPTION OF THE DRAWINGS

The foregoing features of the invention will be more readily understood by reference to the following detailed description, taken with reference to the accompanying drawings, in which:

FIGS. 5(a) and (b) show examples of genes encoding gene expression products for use in panels to measure directed differentiation of cells. FIGS. 5(c) and 5(d) provide the corresponding SEQ ID number for each sequence.

DETAILED DESCRIPTION OF SPECIFIC EMBODIMENTS

Figure 1A:
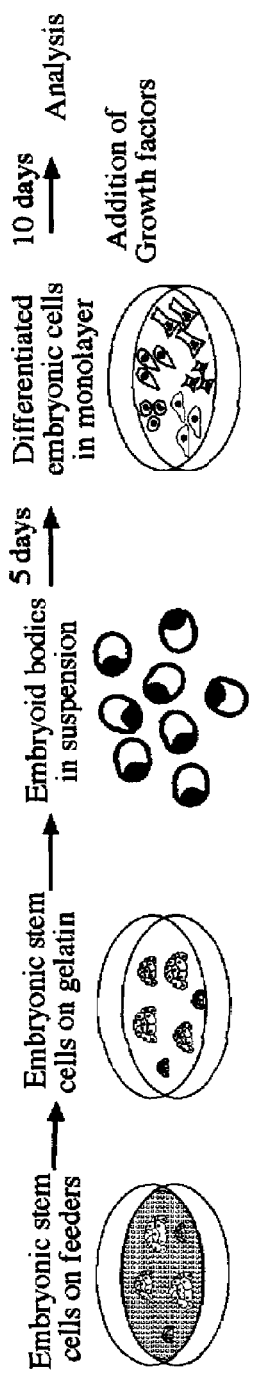
FIG. 1 shows induced differentiation of human embryonic stem cells in culture. (A) A schematic representation of the differentiation protocol. (B) Various morphologies of embryonic stem cells before and after induced differentiation: I: A colony of embryonic stem cells on feeders. II–IV: Differentiated cells cultured in the presence of HGF, Activin-A, RA, bFGF, or BMP-4, respectively also showing the small size of embryonic cells in the colony in comparison to the size of the differentiated cells. Scale bar, 100 µm.

Definitions.

As used in this description and the accompanying claims, the following terms shall have the meanings indicated, unless the context otherwise requires:

The term "differentiation" is defined here and in the claims as a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

The term "embryonic stem cells" as used here and in the claims refers to a pluripotent cell type derived from the inner cell mass of blastocyst stage embryos. The term "embryonic cells" as used here and in the claims includes embryonic stem cells, embryoid bodies (EBs) and differentiated embryonic cells (DE) which are generally pluripotent but may include partially differentiated cells that are multipotent.

The term "exogenous factor" is defined here and in the claims as any factor which when presented in the medium of a population of cells, has an effect on the biological properties of the cell. The term exogenous factor includes a secreted factor or a synthetic agent or a receptor on the surface of a neighboring cell or an inhibitor of any of these. These factors may be proteins, carbohydrates or lipids or mixtures of the same and further may include peptides, non-peptide hormones, small organic molecules and novel therapeutic agents or candidate therapeutic molecules that may be a product of a chemical library or a naturally occurring source. The exogenous factor may be a single type of molecule or a mixture of more than one molecule. The exogenous factor may be purified before being added into the cell medium or it may be a crude preparation. Examples of exogenous factors include secreted biological molecules such as growth factors, hormones, antibodies, as well as salts or ions.

The term "subject" is defined here and in the claims as any living organism, more particularly a mammal, more particularly a human.

The term "gene expression product" is defined here and in the claims as any of a transcribed RNA or a protein including a post translationally modified protein.

The term "a" or "an" or "the" is intended to mean "one or more"

Embodiments of the invention provide a method for screening exogenous factors to determine which are capable of causing directed differentiation of embryonic stem cells into progenitors of mature cells or mature cells themselves. The screening method provides intelligence on how to enrich a population of cells for a particular cell type using a single exogenous factor or combinations of exogenous factors. The method has shown that some exogenous factors have an inhibitory activity with respect to a particular pathway while other factors actively stimulate differentiation down a particular pathway. This latter category may include inhibitors of factors with inhibitory activity. Other factors have no effect on differentiation. The method is exemplified in FIGS. 1 through 4. Further embodiments of the invention utilize gene expression of cell-specific markers as an indicator of cell type that results from differentiation of the embryonic cells in the presence of exogenous factors.

Other embodiments of the invention include selecting exogenous factors that have been found to direct differentiation to produce significantly homogenous cell populations for in vitro or in vivo use. For example, we have found that compared to control differentiated embryonic cells, cultures that are treated with growth factors are more homogeneous and up to half of the culture contained one or two cell types. As exemplified in FIG. 3, panels of gene expression products have been constructed for determining directed differentiation of embryonic cells in the presence of exogenous factors. Using this approach, we can characterize a growing number of partially differentiated and differentiated cell types and can provide a comprehensive profile of exogenous factors suited for inducing a predetermined selection of differentiated cells. A directed differentiation pathway for obtaining neurons from embryonic cells is described in Example 3.

The above described methods are applicable to mammalian embryonic stem cells including human embryonic cells. Prior art references have reported heterogeneous population of murine cells which are enriched for a specific cell either by addition of growth factors or by introduction of transcription factors. (Gordon et al. U.S. Pat. No., 5,914,268; Wiles, et al., (1991) *Development*, Vol. 111, pp. 259–267; Biesecker, et al., (1993) *Exp. Hematol.*, Vol. 21, pp. 774–778; Slager, et al., (1993) *Dev. Genet.*, Vol. 14, pp. 212–224; Bain et al., (1995) *Dev. Biol., Vol.* 168, pp. 342–357; Brustle, et al., (1999) *Science*, Vol. 285, pp. 754–756; Gutierrez-Ramos, et al., (1992) *Proc. Natl. Acad. Sci. USA*, Vol. 89, pp. 9171–9175; Levinson-Dushnik, et al., (1997) *Mol. Cell. Biol.*, Vol. 17, pp. 3817–3822). Subsequent sorting and selection of cell types from the heterogeneous population has been undertaken to further enrich for selected cells. (Klug, et al., (1996) *J. Clin. Invest.*, Vol. 98, pp. 216–224; Kolossov, et al., (1998) *J. Cell. Biol.*, Vol. 143, p.p. 2045–2056; Li, et al., (1998) *Curr. Biol.* 8, Vol. 143, pp. 2045–2056; Lee et al., (2000) *Nature Biotechnology*, Vol. 18, pp. 675–678). Mouse ES cells that are allowed to aggregate to form EBs can differentiate into mature neurons capable of innervating adult mouse brain and spinal chord (Bain et al., (1995) *Dev. Biol.*, Vol. 168, pp. 342–357; Wobus et al., (1988) *Biomed. Biochim. Acta.*, Vol. 47, pp. 965–973; Deacon et al., (1988) *Exp. Neurol.*, Vol. 149, pp. 28–41; Lee et al., (2000) *Nat. Biotechnol.*, Vol. 18, pp. 675–679 and McDonald et al., (1999) *Nat. Med.*, Vol. 5, pp 1410–1412). None of these studies sought to undertake a broad analysis of the effects of a range of exogenous factors on differentiation into multiple cell types.

In a preferred embodiment, we have provided a novel approach for obtaining human differentiated cells from embryonic cells and have established methods to enrich mixtures of multiple cell types (for example, human cell types) in vitro using specific exogenous factors. Utilizing the property of embryonic stem cells for indefinite growth in culture, we describe a means to manipulate differentiation of embryonic stem cells, in particular human embryonic cells, to provide a source of cells for transplantation into a subject. We have found that treatment of dissociated embryoid bodies with exogenous factors can give rise to populations of cells with discrete morphologies such as small cells with pronounced, muscle like syncytiums, neuronal like cells, fibroblast like cells, large round cells or other mesenchymal or epithelial cells. These differing morphologies that suggest that specific programs are initiated as a result of treatment with the factors.

The protocol described in Example 1 for inducing human embryonic stem cell differentiation consisted of an aggregation step which allows complex signaling to occur between the cells (somewhat resembling the gastrulation process) and a dissociation step, after 5 days as EBs, thereby allowing exposure to exogenous growth factors. At the stage of 5 day old EBs, the cells are not terminally differentiated as is evident from their expression of Oct-4, a marker for undifferentiated ES cells and express a wide range of receptors for growth factors.

In the examples, we describe the use of eight growth factors (bFGF, TGFβ1, Activin A, BMP-4, HGF, EGF, βNGF and retinoic acid) for directed differentiation of human embryonic stem cells in vitro. Further examples of exogenous factors include interleukins, hedgehog proteins, vascular endothelial growth factor (VEGF), granulocyte macrophage colony stimulating factor (GMCSF), macrophage colony stimulating factor (MCSF), wnt and int and other members of the FGF family not previously mentioned. Where differentiated human cells express a cell specific receptor for an exogenous factor, the effects of the factor on embryonic stem cells can be monitored by measuring the increased amounts of the cell specific receptors expressed as a result of activation of a differentiation pathway. Differentiation may further be correlated with various epithelial or mesenchymal morphologies. The development of panels for analyzing embryonic cells at various stages of differentiation as described here provide a useful tool for directing differentiation in a routine manner.

Accordingly, in Examples 1 and 2, differentiation of the cells was assayed by expression of 24 cell specific molecular markers that cover all embryonic germ layers and 11 different tissues. The described growth factors are not intended to be limiting. The lineage specific differentiation induced by the various growth factors is summarized in FIG. 4. While each growth factor has a unique effect, we can divide the factors into three categories (FIG. 4) based on their effects on human embryonic stem cell differentiation. The first group (TGFβ1 and Activin-A) appear to inhibit differentiation of cells into endodermal and ectodermal cells, but allow differentiation into selected mesodermal cells. Among mesodermal cells, these factors inhibit differentiation into chondrocytes in the dorsal mesoderm, kidney and Mullerian duct cells in the intermediate mesoderm and blood formation in the lateral mesoderm.

Figure 4:
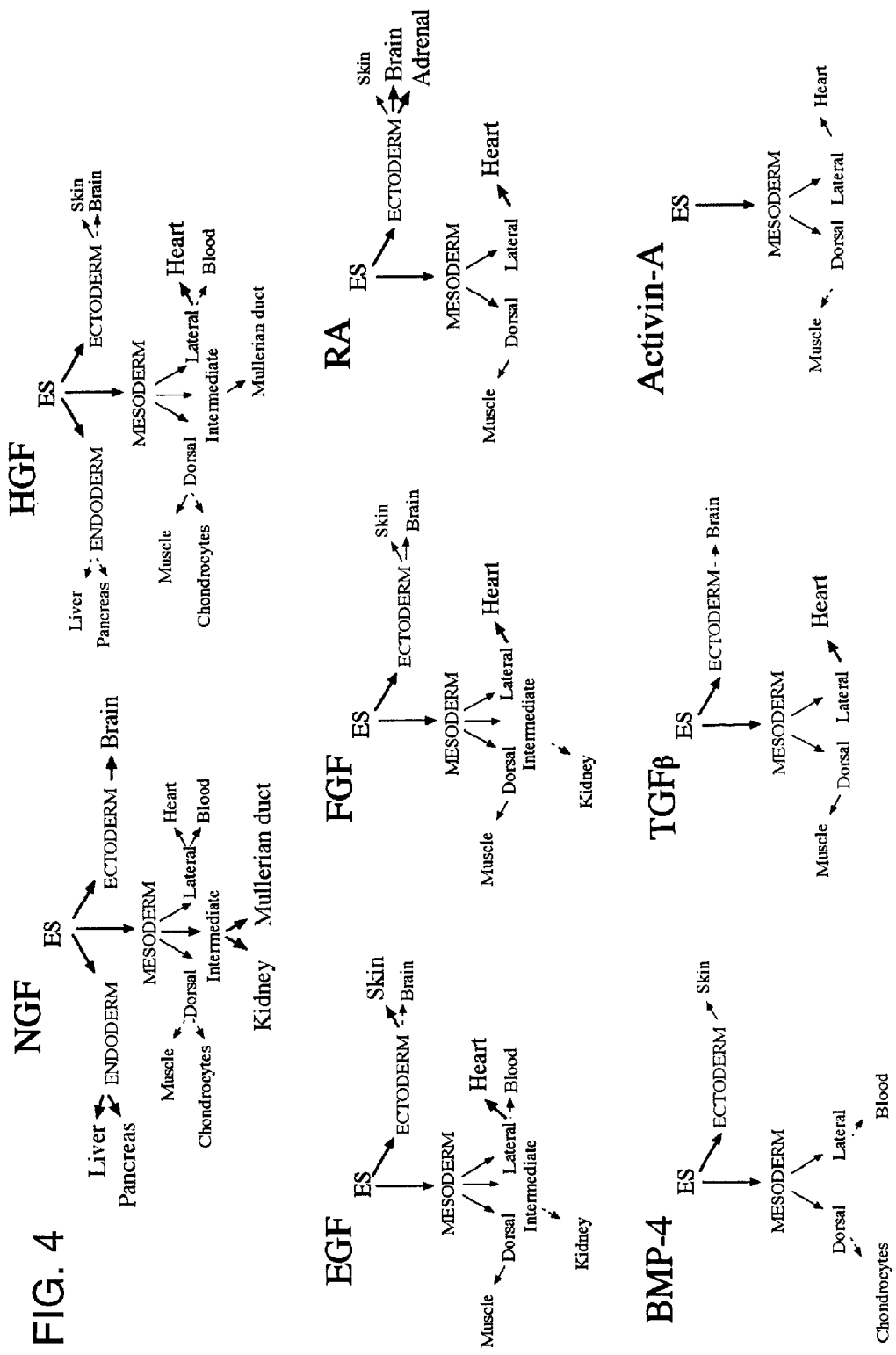
FIG. 4 shows the effects of various growth factors on in vitro differentiation of human embryonic cells. Thick arrows and large fonts indicate an induction compared to the control (no growth factor) for genes specific to the tissue indicated. Dashed arrows represent a decrease in expression. Disappearance of the cell specific transcripts is symbolized by elimination of the corresponding tissue symbol.

The second group includes factors that allow or induce differentiation into ectoderm as well as mesodermal cells (RA, bFGF, BMP-4 and EGF). Nonetheless, these factors vary according to which cells are inhibited, produced at normal levels or enhanced. For example, as shown in FIG. 4, RA inhibits the differentiation of chondrocyte cells, cells produced by the intermediate mesoderm, and blood formation in human embryonic stem cells. In contrast, BMP-4 causes chondrocytes and blood formation differentiation to be reduced and inhibits differentiation of all other mesodermal cells examined while apparently permitting skin cells to form. EGF appears to stimulate differentiation of heart, and skin, permits normal levels of muscle but inhibits the formation of cells forming kidney, blood and brain. FGF stimulates only formation of cells for the heart, permits formation of normal levels of muscle skin and brain and inhibits differentiation of cells for the kidney.

The third group of growth factors (NGF and HGF) allows differentiation into all three embryonic lineages including endoderm. For example, NGF has been shown to direct the differentiation of embryonic cells toward forming liver tissue (hepatocytes), pancreas (islet cells), brain (neurons), kidney and mullerian duct cells. To a lesser extent, NGF appears to stimulate production of heart and blood and to down-regulate differentiation of muscle and bone (chondrocytes). However, differentiation into skin cells is completely inhibited in the presence of NGF. This pattern is not the same for HGF. When HGF is added to human embryonic cells, skin cells are induced at their normal level. However, differentiation of kidney cells is completely inhibited in the presence of HGF, with significant inhibition of formation of liver, pancreas, brain, chondrocytes and blood.

The results provided in FIG. 4 illustrate a powerful new approach to directed differentiation. Any exogenous factor may be analyzed using this approach whereby embryonic stem cells and/or differentiated embryonic cells are exposed to the factor and specific informative gene expression products are analyzed in the differentiated embryonic cells for each of the ectoderm, mesoderm and endodermal tissues and their differentiated counterparts. An advantage of the novel approach to evaluating differentiation of tissues described above is that the complex relationship of a single exogenous factor with respect to differentiation can be established and then manipulated.

For example, specific differentiation in differentiated embryonic (DE) cell cultures can be detected first as a morphological change. After 10 days incubation with an exogenous factor, DE cells were more homogenous and displayed a larger proportion of specific cell types as compared to controls not treated with an exogenous factor. We have analyzed the differentiation of these cells by measuring gene expression using a selected set of markers for different cell types. We have taken advantage of substantial public records of cell mapped proteins. The number of protein markers that are characteristic for mature diseased and healthy cells of different types is very large and provide a convenient starting point for analyzing cells resulting from directed differentiation. Although gene expression products that characterize mature cells are well established, this is not the case for intermediate cell types that occur during differentiation of an undifferentiated embryonic cell to a mature cell. The markers described in FIG. 5 provide examples of gene expression products from which a set of markers may be selected for identifying the effect of an exogenous factor on an embryonic cell population. This list is not intended to be comprehensive. Other markers such as T-cell receptor, α-globin, somatostatin, phosphoenolpyruvate carboxykinase (PEPCK), lactate dehydrogenase (LDH) and G-protein coupled receptors such as glucagon, not previously mentioned can also be used.

The set of markers for intermediate cell lineages may be selected from a group that increases in size in an iterative process. For example, a particular exogenous factor is found to stimulate the differentiation of embryonic cells into a particular type of immature cell recognized by particular markers according to embodiments of the invention. These cells may then be analyzed for protein content by using standard protocols in the art such as 2D protein blots to identify however gene expression varies with the fully mature cells. Those gene expression products that are found in intermediate or mature cells or both may serve as markers for measuring the effect of subsequent exogenous factors on embryonic cells. This approach permits the isolation and characterization of novel precursor cells not previously recognized by prior art methodology.

We have exemplified the above approach using a panel of 24 tissue specific markers from all three germ layers and sub-layers. Eight different growth factors were analyzed on embryonic stem cells in culture using these 24 tissue specific markers. These cells were human although the embodiments of the method may be applied to embryonic stem cells from any source. We utilized the panel of markers in an assay format wherein in one embodiment, the assay format utilized standard quantitative gel based techniques that relied on RT-PCR and selected primers (see Example 1–2 and FIGS. 1–3). Other assay formats known in the art may be used to map pathways of differentiation including sensitive antibody based techniques. Sensitive antibody techniques include radioimmune assays, enzyme linked immune absorption (ELISA) and fluorescent antibody techniques. Other detections means include in situ hybridization methods, and solid chemistry analysis in which probes or primers may be attached to a solid substrate in arrays. DNA arrays permit large numbers of samples to be rapidly analyzed. Accordingly, the effects of the particular growth factors on the differentiation status of multiple tissues in differentiated embryonic cells can be determined.

Figure 1B:
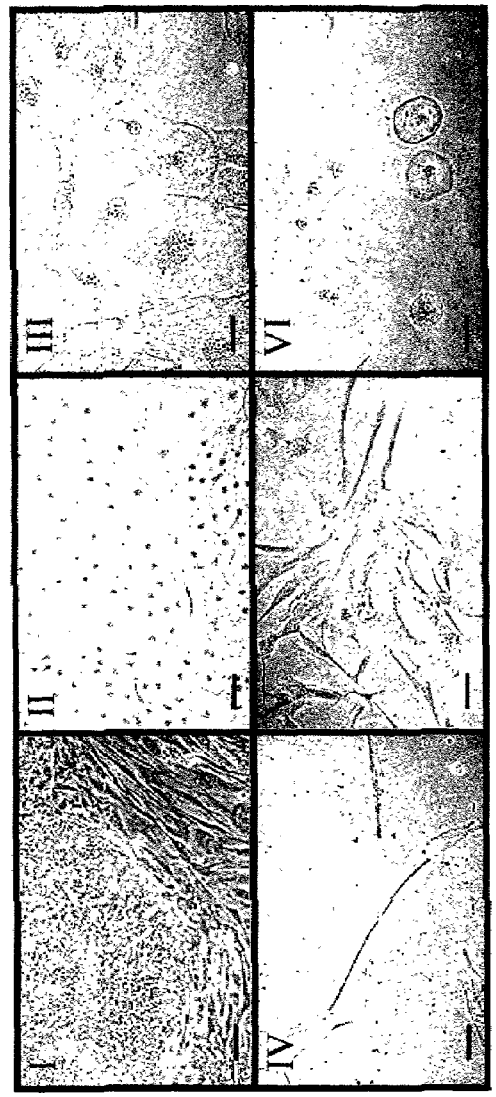
Figure 3A:
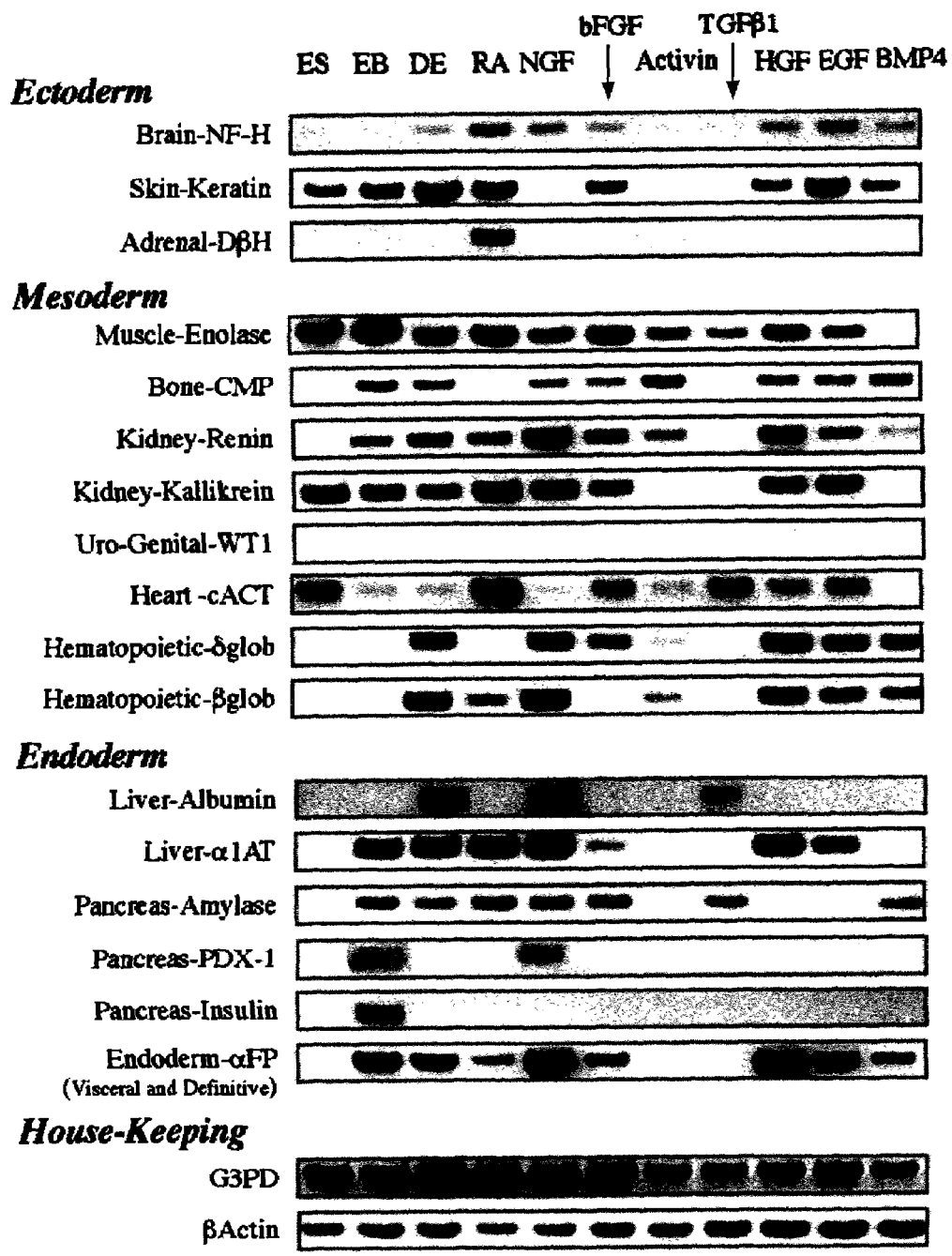
FIG. 3 shows (A) analysis of expression of cell specific genes in human ES cells treated with various growth factors. RNA from ES, 20 day old EBs, and DE cells treated with the different growth factors was analyzed by RT-PCR for expression of seventeen cell specific genes and two housekeeping genes. The genes were categorized by their embryonic germ layer. (B) Schematic representation of the growth factor effects on gene expression. Results are shown from three experiments on the effects of NGF, HGF, EGF, RA, bFGF, BMP4, TGFβ1 or Activin-A on the expression of 13 genes. The results are color-coded: orange represents similar expression to the control (no growth factor), red represents induction of at least two fold, yellow represents inhibition of two fold or more, and green represent no detectable expression.
Figure 3B:
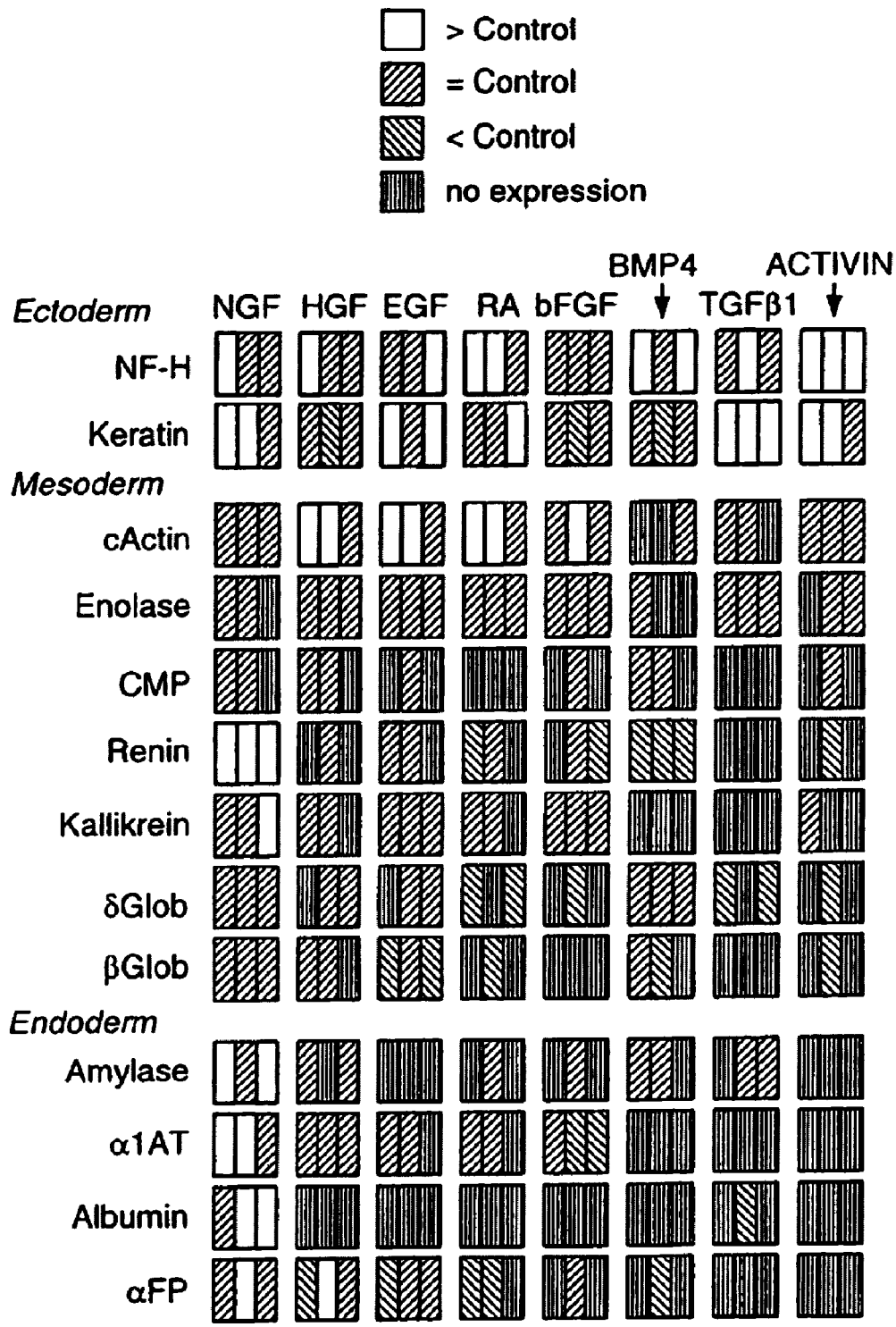

In addition to identifying the expression of genes associated with particular tissues, differentiation can be followed by examining the changing morphology of differentiating cells. For example, the ability to induce specific differentiation was initially evident as morphological changes in the differentiated embryonic cell cultures that had been cultured for predetermined times in the presence of exogenous factors (FIG. 1-A). After incubation with an exogenous factor, differentiated embryonic cells were more homogenous and displayed a larger proportion of specific cell types as compared to controls not treated with factors. The differentiation of these cells was also followed by gene expression studies in which we analyzed the transcription of tissue specific markers from all three germ layers and sub-layers. As shown in Example 2, 16 of the 24 genes examined were expressed in the human DE cells representing 11 different tissues (FIG. 3).

The analysis of a large set of markers permits us to specify factors that can direct differentiation into specific cell types. FIG. 4 shows that none of the eight growth factors tested in the examples directed a completely uniform and singular differentiation of human embryonic stem cells although the number of differentiated cell types varied substantially for different factors. In the above example, differentiation observed from individual growth factors indicates that most of the growth factors tested inhibit differentiation of specific cell types and that this inhibitory effect is more pronounced than an induction effect. Accordingly, specific differentiation may also be achieved by using growth factor inhibitors, such as follistatin or noggin, to counteract endogenous growth factors that might be produced during human embryonic stem cell differentiation.

In summary, certain exogenous factors may primarily inhibit differentiation of cells along certain pathways resulting in differentiation of cells in secondary pathways. Specific tissues may result from withholding or blocking the action of such exogenous factors. Other exogenous factors may directly stimulate differentiation of embryonic stem cells while still other factors may have little or no effect on the growth and development of embryonic stem cells at certain times during development. Multiple factors may be used in a certain order to obtain an optimum differentiation outcome and combined with selection methods provide a means for achieving fully directed cell differentiation.

Embodiments of the invention provide methods for obtaining cells that are differentiated partly or entirely along a particular cell lineage. These methods have both in vivo and in vitro uses. An in vivo use for cells that are a product of an in vitro differentiation pathway could for example be directed to repair of bone damage in vivo using chondrocytes derived from stem cells treated according to methods described herein. Moreover, in vitro differentiated cells may be used to repair damaged organs for example, neuronal cells for spinal cord repair.

We have shown that neurons can be formed from human embryonic cells in the presence of certain growth factors. These neuronal cultures mature to form neuronal processes with varying degrees of complexity. In addition to demonstrating that both RA and βNGF enhance the number of neuronal cells that develop from human embryonic cells as described above, we demonstrate that RA promotes the production of mature neurons and that these neurons express dopamine or serotonin receptors, and form complex plexuses of neuronal processes. Only RA but not NGF induce expression of adrenal markers whereas NGF and not RA induce expression of endodermal markers.

The enrichment of neurons in culture by growth factors may occur through a process of cell selection (either by expansion or improved survival) or as a consequence of induced differentiation. Our production of neuronally-differentiated embryonic cells provides a method for obtaining large amounts of neurons in culture for use for example, in the replacement of neurons lost to degeneration or trauma in the central nervous system in humans. This example serves to underscore the utility of our approach in generating an unlimited source of cells for transplantation therapy and other uses. This can reduce the need for difficult to obtain fetal tissues, which to date are the primary sources of human cells available for transplantation therapy (Peschanski, (1995) *Neuroscience*, Vol. 68, pp. 273–285).

For cell therapy, the cells may be added directly to the subject to reverse an adverse medical condition. For example, differentiated embryonic cells that are neuronal in type may be administered directly to a patient for treating Parkinson's disease, multiple sclerosis or spinal cord injury. Differentiated embryonic cells may be used directly to treat Lou Gehrig's disease, diabetis or other autoimmune condition. Indeed, differentiated embryonic cells may be used directly to treat disease or damage to any organ or tissue in the human body. Alternatively, the cells may be built into an artificial tissue in vitro by seeding a biocompatible three-dimensional or two-dimensional inorganic or organic matrix known in the art with cells and permitting the cells to grow and differentiate within the matrix before transplantation. An example of a biocompatible matrix seeded with adult murine thymic stroma is provided in Poznansky et al., (2000) *Nature Biotechnology*, Vol. 18, pp. 729–734.

Additional uses for methods for providing cells that are differentiated partly or entirely along a particular cell lineage include in vitro uses such as creating reagents for drug toxicity assays. By adding drugs to cultures of differentiated cells such as kidney cells, liver cells, brain cells, heart smooth muscle, chondrocytes, pancreatic cells, neuronal cells, blood cells etc, it is possible to avoid the use of animals in preclinical testing. Furthermore, the addition of drugs to partially differentiated cells may provide useful information on the impact of the drugs on the developing embryo. Isolation and characterization of cells that are intermediate in differentiation provides a useful resource for understanding the genotype and phenotype of cells in development in the context of health and disease.

EXAMPLES

Example 1

Measuring Gene Expression Products In Differentiated Human Embryonic Stem Cells

Cell Culture:

Human embryonic stem cells were grown on a feeder layer of mouse embryonic fibroblasts (MEF) and then transferred to gelatin coated plates and cultured further to reduce the number of murine cells in the culture. Differentiation into embryoid bodies (EBs) was initiated by transfer to petridishes, where the embryoid bodies remained in suspension. After 5 days, the EBs become dissociated and cells are cultured as a monolayer forming differentiated embryonic (DE) cells. This protocol allows for initial differentiation of the human embryonic stem cells as aggregates and further differentiation as a monolayer wherein cells can be exposed to exogenous growth factors. The DE cells were cultured for 10 days in the presence of 8 different growth factors: NGF, bFGF, Activin-A, TGFβ1, HGF, EGF, BMP4 and retinoic acid (RA) (FIG. 1-A).

Human ES cells were obtained as described in Thomson et al., (1998) *Science*, Vol. 286, pp. 1145–1147. Cleavage stage human embryos produced by in vitro fertilization (IVF) were obtained after the requisite approval process. The embryos were cultured to the blastocyst stage and inner cell masses were isolated. ES cell lines were isolated from the embryos and a cell line was selected which had maintained a normal karyotype over a 6 months period of culture and could be passaged continuously over several months without undergoing a period of replicative crisis. The cells had a uniform undifferentiated morphology when grown on mouse embryo fibroblasts in 80% KnockOut™ DMEM—an optimized Dulbeco's modified Eagle's medium for ES cells (Gibco-BRL), 20% KnockOut™ SR—a serum-free formulation (Gibco-BRL), 1 mM glutamine (Gibco-BRL), 0.1 mM β-mercaptoethanol (Sigma), 1% non-essential amino acids stock (Gibco-BRL), $10^3$ units/ml leukemia inhibitor factor (LIF) (Gibco-BRL) and 4 ng/ml basic fibroblast growth factor (bFGF) (Gibco-BRL). Gelatin (0.1%, Merck) was used to cover the tissue culture plates.

To induce formation of EBs, ES cells were transferred using trypsin/EDTA (0.1%/1 mM) to plastic Petri dishes to allow their aggregation and prevent adherence to the plate. Human EBs were grown in the same culture medium, except that it lacked leukemia inhibitory factor (LIF) and bFGF. The EBs were cultured for 5 days and then dissociated and plated on tissue culture plates coated with 50 µg/ml Fibronectin (Boehringer Mannheim). The cells were grown in the presence of the following human recombinant growth factors used singly or in groups: Basic Fibroblast Growth Factor (bFGF) (Swoboda, et.al., (1999) *Neurology*, Vol. 53, pp. 1205–1211.)-10 ng/ml (Gibco BRL). Transforming Growth Factor Beta 1 (TGFβ1) (Swoboda et al.)-2 ng/ml (R&D Systems). Activin-A (Slager et al., (1993) *Dev. Genet.*, Vol. 14, pp. 212–224)-20 ng/ml (R&D Systems). Bone Morphogenic Protein 4 (BMP-4) Slager et al., and Bain et al., (1996) *Biochem. Biophys. Res. Commun.*, Vol. 223, pp. 691–694 14)-10 ng/ml (R&D Systems). Hepatocyte Growth Factor (HGF)/Scatter Factor (Doetsch et al., (1999) *Cell* Vol. 97, pp. 703–716)-20 ng/ml (R&D Systems). Epidermal Growth Factor (EGF) (Doetsch et al.)-100 ng/ml (R&D Systems). βNerve Growth Factor (NGF) (Johansson et al., (1999) *Cell*, Vol., 96, pp. 25–34.)-100 ng/ml (R&D Systems). Retinoic acid (RA) (Deacon, et al., (1998) *Exp. Neurol.* Vol. 149, pp. 28–41; Peschanski, et al., (1995) *Neuroscience*, Vol. 68, pp. 273–285)-1 µM (Sigma). Under these conditions the differentiated embryonic (DE) cells were grown for another 10 days. All of the examined growth factors are absent from the KnockOut™ serum replacement in which the embryonic cells were cultured.

In this example, initial differentiation of the human ES cells aggregates occurred which continued after the cells formed monolayers. In a preferred embodiment, the monolayers were exposed to exogenous factors. FIG. 1-A depicts one protocol that utilizes growth factors.

As described in more detail in Example 2, the presence of receptors which correlate with the addition of exogenous factors could be determined in DE cells at the stage when the factors are added to the culture (5 day old EBs). For example, RNA from human embryonic stem cells, 5 day old EBs and 10 day old DE cells were isolated and analyzed by RT-PCR using primers specific to retinoic acid receptor type alpha (RAR), nerve growth factor receptor (NGFR), fibroblast growth factor receptor type I (FGFRI), activin receptor type IIB (ACTRIIB), transforming growth factor receptor type II (TGFRII), hepatocyte growth factor receptor (c-Met), epidermal growth factor receptor (EGFR), and bone morphogenic protein 4 receptor type II (BMP4RII). As a control, the expression of octamer binding protein 4 (Oct-4), a marker of the undifferentiated cells, and of G3PD (glyceraldehyde 3-phosphate dehydrogenase), a housekeeping gene was also monitored.

In-situ Hybridization and Immunohistochemistry:

EBs or their plated derivatives were fixed in 4% paraformaldehyde. In in-situ experiments, hybridization to a 50-mer 2'-O-methyl 5'-biotinylated cDNA of NF-L (SEQ ID NO: 1) (CCTGCGTGCGGATGGACTTGAGGTCGT-TGCTGATGGCGGCTACCTGGCTC) followed. The probes were then detected with streptavidin-conjugated alkaline phosphatase using a fluorogenic substrate (Grifman, et al., (1998) *Proc. Natl. Acad. Sci. USA*, Vol. 95, pp. 13935–13940). For immunohistochemistry, EBs were either embedded in paraffin and sectioned at 10 µM, or stained directly on the plates. Mouse monoclonal anti-NF-H was used as a primary antibody, and was detected with Cy3-conjugated goat anti-mouse IgG.

RT-PCR Analysis:

Total RNA was extracted using Atlas™ Pure Total RNA Kit (Clontech). cDNA was synthesized from 1 µg total RNA, using Advantage™ RT-for-PCR Kit (Clontech). cDNA samples were subjected to PCR amplification with DNA primers selective for the human genes. For each gene, the DNA primers were derived from different exons to ensure that the PCR product represents the specific mRNA species and not genomic DNA. PCR was performed using the Clontech Advantaq+™ RT-PCR kit and using a 2 step cycle at 60° C.

Primers were synthesized for the following genes: Neurofilament heavy Chain (NF-H), Phosphoprotein enriched in astrocytes (PEA-15), Keratin, Dopamine β Hydroxylase (DβH), Follicular Stimulating Hormone (FSH), Enolase, Myosin light polypeptide2 (myosin), Cartilage Matrix Protein (CMP), Renin, Kallikrein, Wilms Tumor 1 (WT1), β-Globin, (β-Glob), δ-Globin (δ-Glob), Cardiac Actin (cACT), Albumin, α1 anti-trypsin (α1AT), Lipase, Amylase, PDX-1, Insulin, Glucagon, Surfactant, Parathyroid Hormone (PTH), α-feto protein (αFP), Retinoic Acid Receptor type alpha (RAR), Hepatocyte Growth Factor Receptor (c-Met), Nerve Growth Factor Receptor (NGFR), Fibroblast Growth Factor Receptor type I (FGFRI), Transforming Growth Factor Receptor type II (TGFRII), Epidermal Growth Factor Receptor type (EGFR), Activin Receptor type IIB (ACTRIIB), Bone Morphogenic Protein 4 Receptor type II (BMP4RII), Octamer Binding Protein 4 (Oct 4), Glyceraldehyde 3-phosphate dehydrogenase (G3PD), β-Actin. A full description of the primers and their expected products are provided in FIG. 5. Also incorporated by reference, see http://www.ls.huji.ac.il/~nissimb/factors_es/primers.html-ente Example 2

Figure 2:
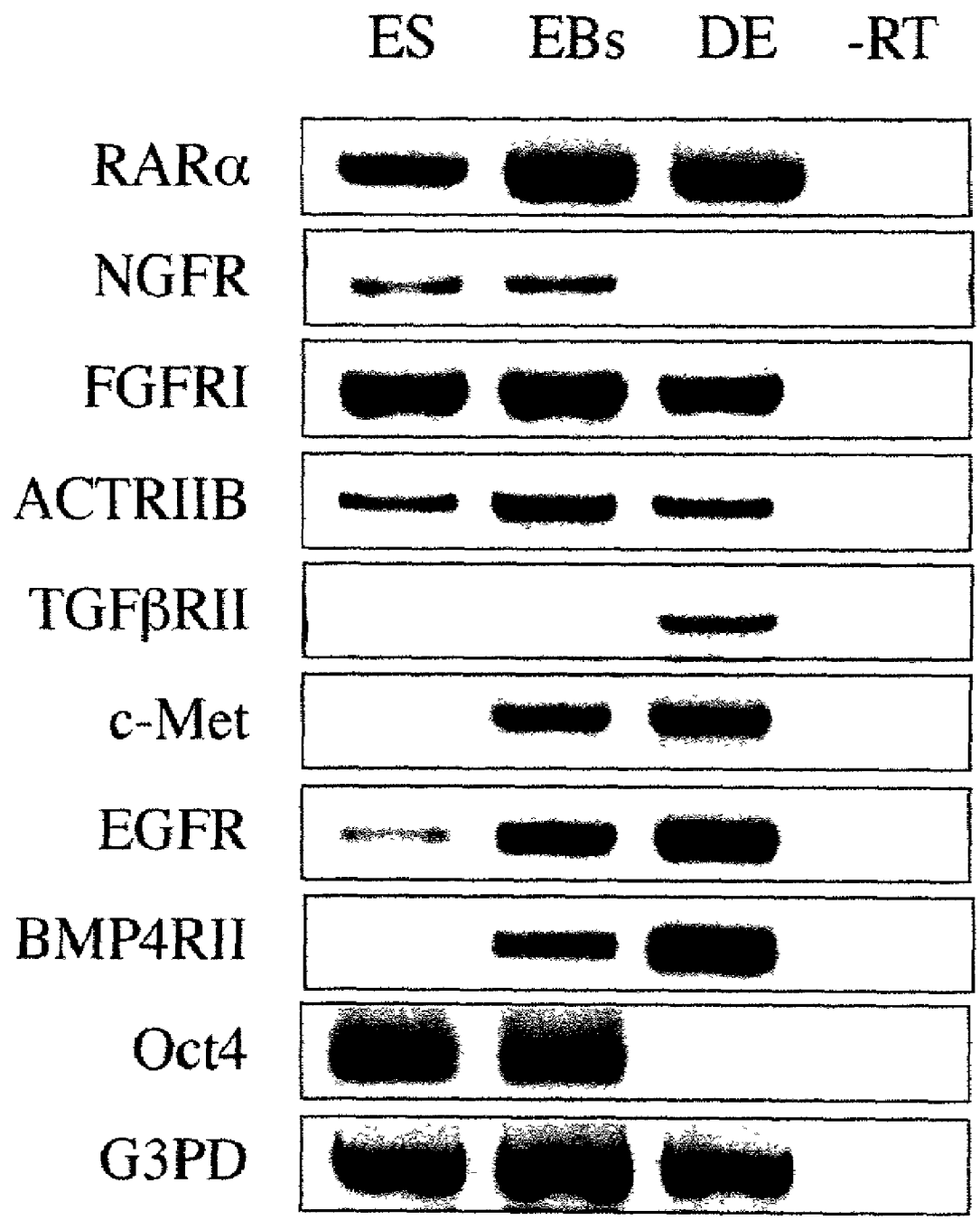
FIG. 2 shows expression of receptors for various growth factors in human embryonic stem cells. RNA samples from ES cells, 5 day old embryoid bodies (EBs) and differentiated embryonic (DE) cells were analyzed by RT-PCR for expression of specific receptors. As a control, RNA of 5 day old EBs was analyzed without the prior generation of cDNA (–RT).

Mapping Pathways Of Differentiation By Measuring The Effect Of Exogenous Growth Factors On Undifferentiated Cells All 8 target receptors were expressed in 5 day old EBs and most were expressed in ES and DE cells (FIG. 2). Notably, four of the receptors (TGFRII, c-Met, EGFR and BMP4RII) were expressed at very low levels in human ES cells and their expression increases following culture and further differentiation. Without wishing to be limited by theory, we propose that low levels of expression may result from partial differentiation in embryonic cell cultures.

Since growth factor receptors were expressed in 5 day old EBs, we could examine the effects of the corresponding ligands on differentiation. After several days of culture on plastic and continuous exposure to growth factors, the cells acquired different morphologies (FIG. 1-B). Without growth factors, cells spontaneously differentiated into many different types of colonies, whereas the addition of growth factors produced more mature cell morphologies such as syncitial myocytes and neuronal cells. Compared to control DE cells, the growth factor treated cultures were more homogenous and up to half of the culture contained one or two cell types. For example, large populations of small cells with pronounced nuclei were found in cultures treated with HGF (FIG. 1-B-I), muscle like syncitiums in the Activin-A treated cells (FIG. 1-B-III), neuronal like cells in the RA treated culture (FIG. 1-B-IV), fibroblast like cells in the cultures treated with bFGF (FIG. 1-B-V), and large round cells in cultures treated with BMP-4 (FIG. 1-B-VI). These varied cell morphologies demonstrate that specific programs are initiated as a result of growth factor treatment.

The differentiation induced by growth factors was further examined by determining the expression of a panel of 24 cell specific genes using RT-PCR. RNA was isolated from ES cells, 20 day old EBs, 10 day old DE cells, and DE cells that had been treated with either RA, NGF, bFGF, Activin-A, TGFβ1, HGF, EGF, and BMP4. Complementary DNA was generated from the various samples and transcripts were amplified by specific primers to these genes. For each gene, the two DNA primers were derived from different exons to ensure that the PCR product represented the specific mRNA species and not genomic DNA. In addition, the correct product of amplification from the primers was ascertained by amplifying cDNAs from a variety of human adult or embryonic tissues (Clontech, MTC™ Panels) (results not shown). Out of the 24 cell specific markers, 16 were expressed in the treated DE cells. Most transcripts were also expressed in the control DE cells (see FIG. 3-A), indicating that many different cell types develop from ES cells without a requirement of exogenous growth factors. Moreover, human embryonic cell cultures expressed some cell specific genes, indicating that there is partial spontaneous differentiation in the cultures.

Several conclusions can be drawn comparing the expression pattern of cell specific markers in the different treatments to that of the control DE cells. Some markers are expressed only in a presence of a specific growth factor, e.g. the adrenal marker dopamine β hydroxylase (DβH) is expressed only when the cells are treated with retinoic acid and the uro-genital marker WT-1 is expressed when either NGF or HGF are added (FIG. 3-A). In contrast, muscle specific enolase is expressed under all conditions except following BMP-4 exposure (FIG. 3-A). Some growth factors, e.g. NGF, induce expression of a variety of transcripts indicative of cells from all three germ layers whereas other factors, i.e. TGFβ1, lead to the production of a relatively reduced set of specific transcripts.

Each of the growth factor induction experiments was repeated at least three times. RT-PCR analysis was performed and a schematic representation of the results is shown in FIG. 3-B. Induction or repression of gene expression is color-coded and the growth factors were ordered based on their overall induction or repression of cell specific expression. Thus, on the left is the factor (NGF) that induces the greatest variety of cell specific gene expression of the factors tested, and on the right are the factors (BMP-4, Activin-A and TGFβ1) that mostly repress or fail to direct differentiation of as many cell types.

Example 3

Characterizing Derivative Cells From Ebs For Neuronal Differentiation

Cell Culture.

Human ES cells were grown and EBs were generated as described in Example 1. Four days following initiation of aggregation growth factors were administered: retinoic acid (Sigma): $10^{-7}$M (Bain et al (1995) or $10^{-6}$M (Bain et al., 1996); TGFβ1 (Sigma): 2 ng/ml (Slager et al., (1993) *Dev. Genet.*, Vol.14, pp. 212–224.); βNGF (New Biotechnology, Israel): 100 ng/ml (Wobus et al., 1988). After 21 days, EBs were plated on 5 μg/cm² collagen treated plates, either as whole EB's, or as single cells dissociated with trypsin/EDTA. The cultures were maintained for an additional week or 2 days respectively.

Figure 6:
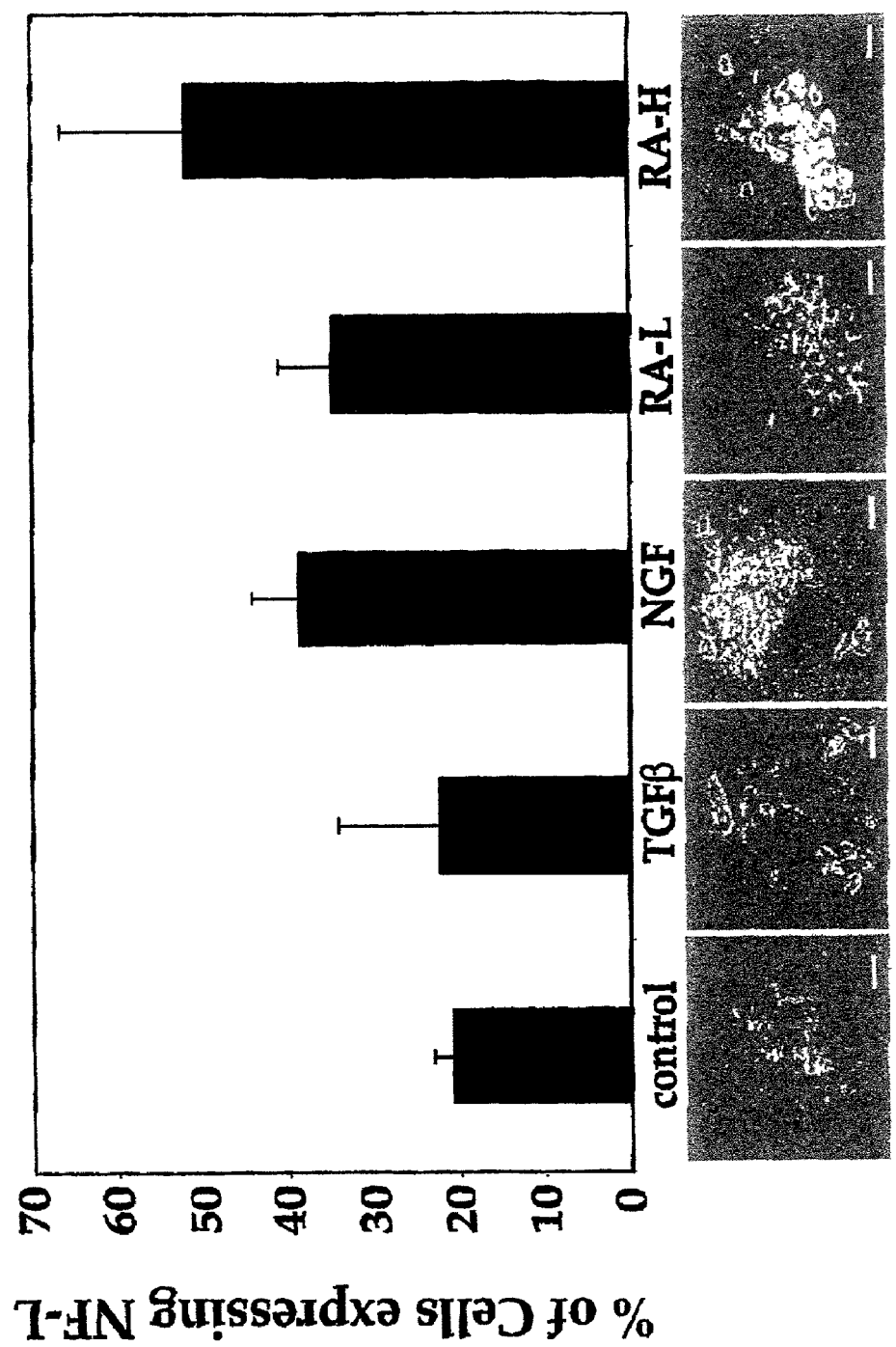
FIG. 6 shows that retinoic acid and, βNGF induce expression of neurofilament light chain (NF-L) mRNA. In situ hybridization analysis of cells derived from dissociated EBs demonstrating expression of NF-L. Shown are RA-(low ($10^{-7}$M) or high ($10^{-6}$M) concentrations), TGFβ1, and βNGF-treated cultures. Scale Bar=100 µM. Histograms show the percentage of cells expressing the NF-L RNA following each treatment. Assay of each condition was repeated three times (between 50 to 150 cells) and standard error bars are shown in the graph.

In-situ hybridization and immunohistochemistry was carried out according to Example 1. RT-PCR analysis. cDNA was synthesized from total RNA and PCR performed according to Example 1. Primers for GAPDH, serotonin receptors 2A and 5A (5HT2A, 5HT5A respectively) and dopamine receptor D1 (DRD1) were purchased from Clontech. The primers for dopa decarboxylase (DDC) were: (SEQ ID NO:2) TCTGTGCCTCTTAACTGTCACTGTGG and (SEQ ID NO: 3) ATCATCACAGTCTCCAGCTCTGTGC. The results are shown in FIGS. 6–8.

Differentiation was initially assayed by in-situ hybridization to neurofilament light chain (NF-L) RNA, which is expressed by both immature and fully differentiated neurons (M. J. Carden, et al., (1987) *J. Neurosci.*, Vol. 7, pp.

3489–3504). We found that βNGF and high concentration of RA increased the proportion of neuronal cells in the cultures from 21% in controls to 39% and 52% respectively. A lower concentration of RA ($10^{-7}$M instead of $10^{-6}$M) produced an effect similar to NGF, whereas no effect on neuronal differentiation was observed with TGFβ1 treatment (FIG. 6).

Figure 7A:
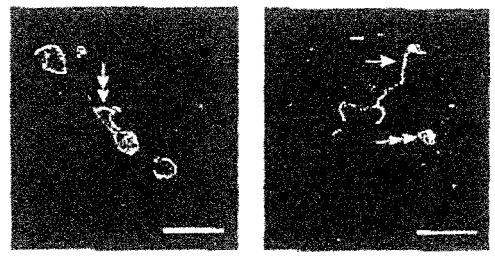
FIG. 7 shows that retinoic acid enhances formation of neuronal processes from human EBs. (A) neuronal cell bodies (double arrows) and a complex proximal process (arrow) are seen in a section through an EB stained with anti-NF-H antibody. Hoecsht staining (blue) shows both intact and fragmented nuclei. (B) A plexus of neuronal-like processes formed from intact EBs plated on collagen. (C) Immunostaining for NF-H of 20 day old EBs plated on collagen shows that plexuses of neuronal processes with varying degrees of complexity develop. (D) A histogram summarizing the effect of RA on the proportion of EBs displaying different degrees of network complexity. Each condition was assayed by counting all EBs in culture (between 20 to 40) and the experiment was repeated twice resulting in similar results. Scale Bar=100 µM.
Figure 7B:
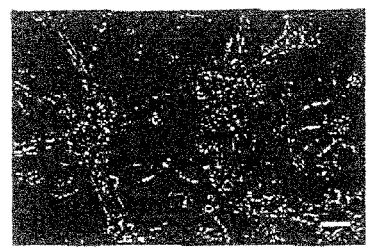
Figure 7C:
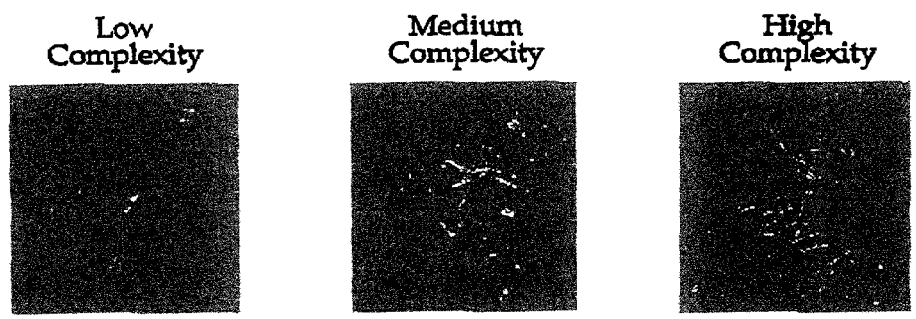
Figure 7D:
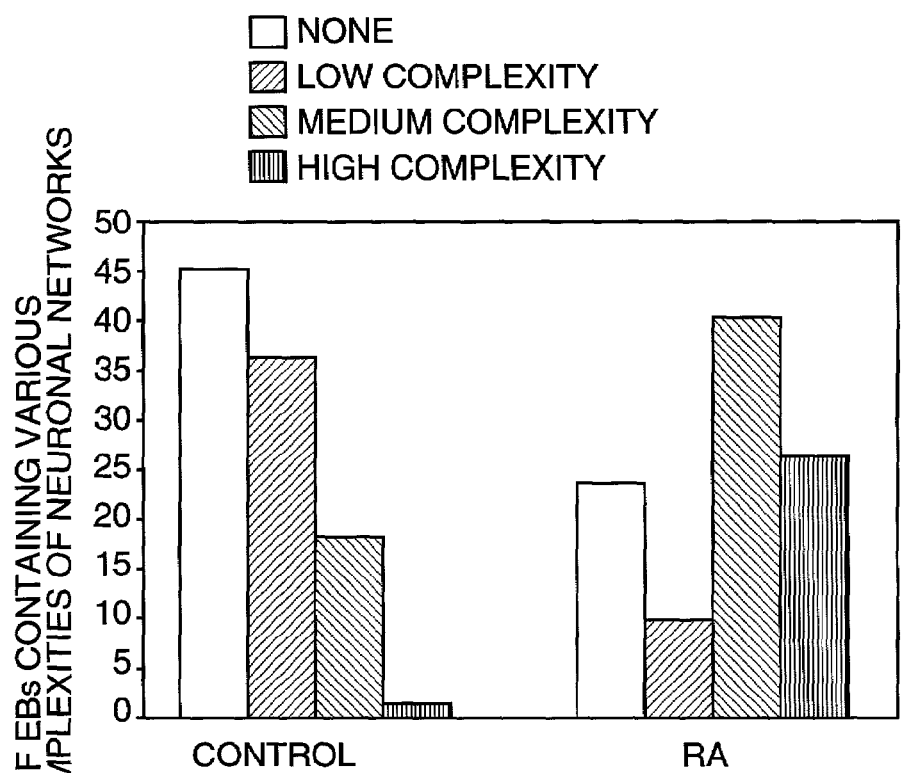
Figure 8:
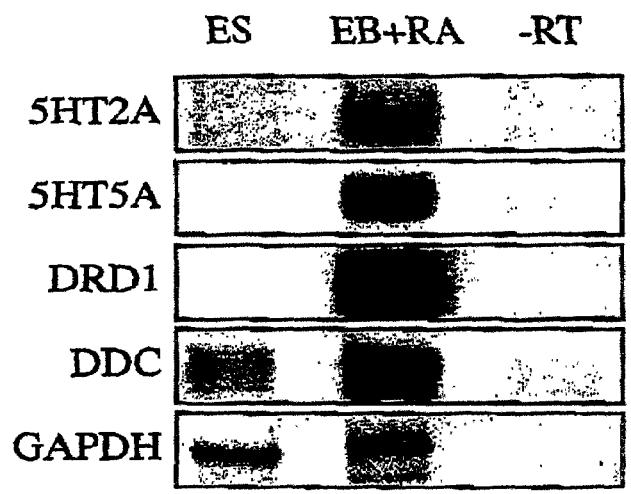
FIG. 8 shows that retinoic acid induces expression of neuron-specific genes. RT-PCR analysis of expression of dopamine receptor D1 (DRD1), serotonin receptor 2A and 5A (5HT2A and 5HT5A), dopa decarboxylase (DDC) and the house-keeping gene glyceraldehyde-3-phosphate dehydrogenase (GAPDH) in human embryonic stem (ES) cells, and in 21 day old EBs in the presence of RA (EB+RA). RNA samples that were not reverse transcribed were used as a negative control to ensure the absence of DNA contamination (-RT).

Immunostaining revealed neurofilament heavy chain (NF-H) protein, found only in mature neurons (Carden et al.), in sections of mature EBs (FIG. 7a). When the EBs were plated, these neurons formed filamentous "networks" (FIG. 7b) of various complexities which were stained positive for NF-H (FIG. 7c). Treatment with RA and consequent plating caused an increase in the number of EBs containing NF-H positive neurons to 76%, compared to 54% in untreated EB's. Moreover, the RA-treated EBs showed dramatic shift towards more complex network morphology (FIG. 7d) suggesting a positive effect of the growth factor on the differentiation status of the cells.

To further characterize the nerve cells obtained from human ES cells, we assayed for expression of a dopamine receptor (DRD1) and two serotonin receptors (5HT2A and 5HT5A) in EBs treated with RA and in ES cells as a negative control (FIG. 8). These receptors were detected in EBs following RA treatment, but not in naive ES cells. Since dopamine and serotonin receptors were expressed, it was interesting to determine whether neurons in the cultures also synthesized their neurotransmitter ligands. Consistent with this possibility, we observed the expression of dopa decarboxylase (DDC) a key enzyme in the synthesis of both serotonin and dopamine (Swoboda et al., (1999) *Neurology*, Vol. 53, pp. 1205–1211) (FIG. 8).

All references recited above are herein incorporated by reference. The particular embodiments of the invention described above are not intended to limit the scope of the present invention which will be limited only by the appended claims.

What is claimed is:

1. A method of directing differentiation of human embryonic cells to human neuronal cells comprising:
   a. providing chemically dissociated human embryonic stem (hES) cells;
   b. aggregating the dissociated hES cells in suspension in to form embryoid bodies;
   c. dissociating the embryoid bodies to provide dissociated single embryonic cells;
   d. culturing said dissociated embryonic cells as a monolayer; and
   e. exposing said embryonic cells to at least one exogenous factor for an effective period of time to direct differentiation of said dissociated embryonic cells to neuronal cells.

2. A method according to claim 1, wherein the embryoid bodies are formed in a suspension culture.

3. A method according to claim 1, wherein the exogenous factor is a growth factor.

4. A method according to claim 3, wherein the exogenous factor is nerve growth factor.

5. A method according to claim 1, wherein the exogenous factor is retinoic acid.

6. A method according to claim 1, wherein the differentiated cells have neuronal processes.

* * * * *

SEQUENCE LISTING

<160> NUMBER OF SEQ ID NOS: 73

<210> SEQ ID NO 1
<211> LENGTH: 50
<212> TYPE: DNA
<213> ORGANISM: Homo sapien
<220> FEATURE:
<223> OTHER INFORMATION: 50-mer 2'-O-methyl 5-biotinylated cDNA probe of
      NF-L

<400> SEQUENCE: 1
cctgcgtgcg gatggacttg aggtcgttgc tgatggcggc tacctggctc           50

<210> SEQ ID NO 2
<211> LENGTH: 26
<212> TYPE: DNA
<213> ORGANISM: Homo sapien
<220> FEATURE:
<223> OTHER INFORMATION: DNA primer for human dopa decarboxylase

<400> SEQUENCE: 2
tctgtgcctc ttaactgtca ctgtgg                                     26

<210> SEQ ID NO 3
<211> LENGTH: 25
<212> TYPE: DNA
<213> ORGANISM: Homo sapien
<220> FEATURE:
<223> OTHER INFORMATION: DNA primer for human dopa decarboxylase

<400> SEQUENCE: 3
atcatcacag tctccagctc tgtgc                                      25

<210> SEQ ID NO 4
<211> LENGTH: 20
<212> TYPE: DNA
<213> ORGANISM: Homo sapien
<220> FEATURE:
<223> OTHER INFORMATION: 5' primer of alpha-feto protein

<400> SEQUENCE: 4
agaacctgtc acaagctgtg                                            20

<210> SEQ ID NO 5

```
<211> LENGTH: 20
<212> TYPE: DNA
<213> ORGANISM: Homo sapien
<220> FEATURE:
<223> OTHER INFORMATION: 3' primer of alpha-feto protein

<400> SEQUENCE: 5
gacagcaagc tgaggatgtc                                              20

<210> SEQ ID NO 6
<211> LENGTH: 25
<212> TYPE: DNA
<213> ORGANISM: Homo sapien
<220> FEATURE:
<223> OTHER INFORMATION: 5' primer of alpha 1 anti-trypsin

<400> SEQUENCE: 6 agacccttctg aagtcaagga caccg                                        25

<210> SEQ ID NO 7
<211> LENGTH: 25
<212> TYPE: DNA
<213> ORGANISM: Homo sapien
<220> FEATURE:
<223> OTHER INFORMATION: 3' primer of alpha 1 anti-trypsin

<400> SEQUENCE: 7
ccattgctga agaccttagt gatgc                                         25

<210> SEQ ID NO 8
<211> LENGTH: 25
<212> TYPE: DNA
<213> ORGANISM: Homo sapien
<220> FEATURE:
<223> OTHER INFORMATION: 5' primer of Activin Receptor type 11B

<400> SEQUENCE: 8
acacgggagt gcatctacta caacg                                         25

<210> SEQ ID NO 9
<211> LENGTH: 25
<212> TYPE: DNA
<213> ORGANISM: Homo sapien
<220> FEATURE:
<223> OTHER INFORMATION: 3' primer of Activin Receptor type 11B

<400> SEQUENCE: 9
ttcatgagct gggccttcca gacac                                         25

<210> SEQ ID NO 10
<211> LENGTH: 26
<212> TYPE: DNA
<213> ORGANISM: Homo sapien
<220> FEATURE:
<223> OTHER INFORMATION: 5' primer of Albumin

<400> SEQUENCE: 10
cctttggcac aatgaagtgg gtaacc                                        26

<210> SEQ ID NO 11
<211> LENGTH: 25
<212> TYPE: DNA
<213> ORGANISM: Homo sapien
<220> FEATURE:
<223> OTHER INFORMATION: 3' primer of Albumin

<400> SEQUENCE: 11
```
cagcagtcag ccatttcacc atagg                                      25

<210> SEQ ID NO 12
<211> LENGTH: 25
<212> TYPE: DNA
<213> ORGANISM: Homo sapien
<220> FEATURE:
<223> OTHER INFORMATION: 5' primer of Amylase

<400> SEQUENCE: 12
gctgggctca gtattcccca aatac                                      25

<210> SEQ ID NO 13
<211> LENGTH: 25
<212> TYPE: DNA
<213> ORGANISM: Homo sapien
<220> FEATURE:
<223> OTHER INFORMATION: 3' primer of Amylase

<400> SEQUENCE: 13
gacgacaatc tctgacctga gtagc                                      25

<210> SEQ ID NO 14
<211> LENGTH: 25
<212> TYPE: DNA
<213> ORGANISM: Homo sapien
<220> FEATURE:
<223> OTHER INFORMATION: 5' primer of Beta-Actin

<400> SEQUENCE: 14
tggcaccaca ccttctacaa tgagc                                      25

<210> SEQ ID NO 15
<211> LENGTH: 25
<212> TYPE: DNA
<213> ORGANISM: Homo sapien
<220> FEATURE:
<223> OTHER INFORMATION: 3' primer of Beta-Actin

<400> SEQUENCE: 15
gcacagcttc tccttaatgt cacgc                                      25

<210> SEQ ID NO 16
<211> LENGTH: 25
<212> TYPE: DNA
<213> ORGANISM: Homo sapien
<220> FEATURE:
<223> OTHER INFORMATION: 5' primer of Beta-Globin

<400> SEQUENCE: 16
acctgactcc tgaggagaag tctgc                                      25

<210> SEQ ID NO 17
<211> LENGTH: 25
<212> TYPE: DNA
<213> ORGANISM: Homo sapien
<220> FEATURE:
<223> OTHER INFORMATION: 3' primer of Beta-Globin

<400> SEQUENCE: 17
tagccacacc agccaccact ttctg                                      25

<210> SEQ ID NO 18
<211> LENGTH: 25
<212> TYPE: DNA

<213> ORGANISM: Homo sapien
<220> FEATURE:
<223> OTHER INFORMATION: 5' primer of Bone Morphogenic Protein 4 Receptor type 11

<400> SEQUENCE: 18
tctgcagcta ggtcctctca tcagc                                              25

<210> SEQ ID NO 19
<211> LENGTH: 25
<212> TYPE: DNA
<213> ORGANISM: Homo sapien
<220> FEATURE:
<223> OTHER INFORMATION: 3' primer of Bone Morphogenic Protein 4 Receptor type 11

<400> SEQUENCE: 19
tatactgctc catatcgacc tcggc                                              25

<210> SEQ ID NO 20
<211> LENGTH: 20
<212> TYPE: DNA
<213> ORGANISM: Homo sapien
<220> FEATURE:
<223> OTHER INFORMATION: 5' primer of Cardiac Actin

<400> SEQUENCE: 20
tctatgaggg ctacgctttg                                                    20

<210> SEQ ID NO 21
<211> LENGTH: 20
<212> TYPE: DNA
<213> ORGANISM: Homo sapien
<220> FEATURE:
<223> OTHER INFORMATION: 3' primer of Cardiac Actin

<400> SEQUENCE: 21
cctgactgga aggtagatgg                                                    20

<210> SEQ ID NO 22
<211> LENGTH: 25
<212> TYPE: DNA
<213> ORGANISM: Homo sapien
<220> FEATURE:
<223> OTHER INFORMATION: 5' primer of Cartilage Matrix Protein

<400> SEQUENCE: 22
atgactgtga gcaggtgtgc atcag                                              25

<210> SEQ ID NO 23
<211> LENGTH: 25
<212> TYPE: DNA
<213> ORGANISM: Homo sapien
<220> FEATURE:
<223> OTHER INFORMATION: 3' primer of Cartilage Matrix Protein

<400> SEQUENCE: 23
ctggttgatg gtcttgaagt cagcc                                              25

<210> SEQ ID NO 24
<211> LENGTH: 25
<212> TYPE: DNA
<213> ORGANISM: Homo sapien
<220> FEATURE:
<223> OTHER INFORMATION: 5' primer of Delta-Globin

<400> SEQUENCE: 24
accatggtgc atctgactcc tgagg                                              25

-continued

<210> SEQ ID NO 25
<211> LENGTH: 25
<212> TYPE: DNA
<213> ORGANISM: Homo sapien
<220> FEATURE:
<223> OTHER INFORMATION: 3' primer of Delta-Globin

<400> SEQUENCE: 25
acttgtgagc caaggcatta gccac                                              25

<210> SEQ ID NO 26
<211> LENGTH: 26
<212> TYPE: DNA
<213> ORGANISM: Homo sapien
<220> FEATURE:
<223> OTHER INFORMATION: 5' primer of Dopamine Beta Hydroxylase

<400> SEQUENCE: 26
cacgtactgg tgctacatta aggagc                                             26

<210> SEQ ID NO 27
<211> LENGTH: 25
<212> TYPE: DNA
<213> ORGANISM: Homo sapien
<220> FEATURE:
<223> OTHER INFORMATION: 3' primer of Dopamine Beta Hydroxylase

<400> SEQUENCE: 27
aatggccatc actggcgtgt acacc                                              25

<210> SEQ ID NO 28
<211> LENGTH: 24
<212> TYPE: DNA
<213> ORGANISM: Homo sapien
<220> FEATURE:
<223> OTHER INFORMATION: 5' primer of Enolase

<400> SEQUENCE: 28
tgacttcaag tcgcctgatg atcc                                               24

<210> SEQ ID NO 29
<211> LENGTH: 25
<212> TYPE: DNA
<213> ORGANISM: Homo sapien
<220> FEATURE:
<223> OTHER INFORMATION: 3' primer of Enolase

<400> SEQUENCE: 29
tgcgtccagc aaagattgcc ttgtc                                              25

<210> SEQ ID NO 30
<211> LENGTH: 26
<212> TYPE: DNA
<213> ORGANISM: Homo sapien
<220> FEATURE:
<223> OTHER INFORMATION: 5' primer of Epidermal Growth Factor Receptor
      type

<400> SEQUENCE: 30
cagtcgtcag cctgaacata acatcc                                             26

<210> SEQ ID NO 31
<211> LENGTH: 25
<212> TYPE: DNA
<213> ORGANISM: Homo sapien

```
<220> FEATURE:
<223> OTHER INFORMATION: 3' primer of Epidermal Growth Factor Receptor
      type

<400> SEQUENCE: 31
aggttgcact tgtccacgca ttccc                                              25

<210> SEQ ID NO 32
<211> LENGTH: 26
<212> TYPE: DNA
<213> ORGANISM: Homo sapien
<220> FEATURE:
<223> OTHER INFORMATION: 5' primer of Fibroblast Growth Factor Receptor
      type I

<400> SEQUENCE: 32
agcatcataa tggactctgt ggtgcc                                             26

<210> SEQ ID NO 33
<211> LENGTH: 25
<212> TYPE: DNA
<213> ORGANISM: Homo sapien
<220> FEATURE:
<223> OTHER INFORMATION: 3' primer of Fibroblast Growth Factor Receptor
      type I

<400> SEQUENCE: 33
agtccgatag agttacccgc caagc                                              25

<210> SEQ ID NO 34
<211> LENGTH: 25
<212> TYPE: DNA
<213> ORGANISM: Homo sapien
<220> FEATURE:
<223> OTHER INFORMATION: 5' primer of Follicular Stimulating Hormone

<400> SEQUENCE: 34
gtgagctgac caacatcacc attgc                                              25

<210> SEQ ID NO 35
<211> LENGTH: 25
<212> TYPE: DNA
<213> ORGANISM: Homo sapien
<220> FEATURE:
<223> OTHER INFORMATION: 3' primer of Follicular Stimulating Hormone

<400> SEQUENCE: 35
tttcaccaaa ggagcagtag ctggg                                              25

<210> SEQ ID NO 36
<211> LENGTH: 25
<212> TYPE: DNA
<213> ORGANISM: Homo sapien
<220> FEATURE:
<223> OTHER INFORMATION: 5' primer of Glucagen

<400> SEQUENCE: 36
ctcagtgatc ctgatcagat gaacg                                              25

<210> SEQ ID NO 37
<211> LENGTH: 25
<212> TYPE: DNA
<213> ORGANISM: Homo sapien
<220> FEATURE:
<223> OTHER INFORMATION: 3' primer of Glucagen

<400> SEQUENCE: 37
```
agtccctggc ggcaagatta tcaag                                             25

<210> SEQ ID NO 38
<211> LENGTH: 26
<212> TYPE: DNA
<213> ORGANISM: Homo sapien
<220> FEATURE:
<223> OTHER INFORMATION: 5' primer of Glyceraldehyde 3-phosphate
      dehydrogenase

<400> SEQUENCE: 38
tgaaggtcgg agtcaacgga tttggt                                            26

<210> SEQ ID NO 39
<211> LENGTH: 24
<212> TYPE: DNA
<213> ORGANISM: Homo sapien
<220> FEATURE:
<223> OTHER INFORMATION: 3' primer of Glyceraldehyde 3-phosphate
      dehydrogenase

<400> SEQUENCE: 39
catgtgggcc atgaggtcca ccac                                              24

<210> SEQ ID NO 40
<211> LENGTH: 26
<212> TYPE: DNA
<213> ORGANISM: Homo sapien
<220> FEATURE:
<223> OTHER INFORMATION: 5' primer of Hepatocyte Growth Factor Receptor

<400> SEQUENCE: 40
agaaattcat caggctgtga agcgcg                                            26

<210> SEQ ID NO 41
<211> LENGTH: 25
<212> TYPE: DNA
<213> ORGANISM: Homo sapien
<220> FEATURE:
<223> OTHER INFORMATION: 3' primer of Hepatocyte Growth Factor Receptor

<400> SEQUENCE: 41
ttcctccgat cgcacacatt tgtcg                                             25

<210> SEQ ID NO 42
<211> LENGTH: 24
<212> TYPE: DNA
<213> ORGANISM: Homo sapien
<220> FEATURE:
<223> OTHER INFORMATION: 5' primer of Insulin

<400> SEQUENCE: 42
ctgcatcaga agaggccatc aagc                                              24

<210> SEQ ID NO 43
<211> LENGTH: 25
<212> TYPE: DNA
<213> ORGANISM: Homo sapien
<220> FEATURE:
<223> OTHER INFORMATION: 3' primer of Insulin

<400> SEQUENCE: 43
ggctttattc catctctctc ggtgc                                             25

<210> SEQ ID NO 44

```
<211> LENGTH: 25
<212> TYPE: DNA
<213> ORGANISM: Homo sapien
<220> FEATURE:
<223> OTHER INFORMATION: 5' primer of Kallikrein

<400> SEQUENCE: 44
gttcatgtca gtgagagctt cccac                                         25

<210> SEQ ID NO 45
<211> LENGTH: 25
<212> TYPE: DNA
<213> ORGANISM: Homo sapien
<220> FEATURE:
<223> OTHER INFORMATION: 3' primer of Kallikrein

<400> SEQUENCE: 45
tcacataaga cagcactctg acggc                                         25

<210> SEQ ID NO 46
<211> LENGTH: 25
<212> TYPE: DNA
<213> ORGANISM: Homo sapien
<220> FEATURE:
<223> OTHER INFORMATION: 5' primer of Keratin

<400> SEQUENCE: 46
aggaaatcat ctcaggagga agggc                                         25

<210> SEQ ID NO 47
<211> LENGTH: 25
<212> TYPE: DNA
<213> ORGANISM: Homo sapien
<220> FEATURE:
<223> OTHER INFORMATION: 3' primer of Keratin

<400> SEQUENCE: 47
aaagcacaga tcttcgggag ctacc                                         25

<210> SEQ ID NO 48
<211> LENGTH: 24
<212> TYPE: DNA
<213> ORGANISM: Homo sapien
<220> FEATURE:
<223> OTHER INFORMATION: 5' primer of Lipase

<400> SEQUENCE: 48
gattcatcaa gcatcagtgg ctcc                                          24

<210> SEQ ID NO 49
<211> LENGTH: 25
<212> TYPE: DNA
<213> ORGANISM: Homo sapien
<220> FEATURE:
<223> OTHER INFORMATION: 3' primer of Lipase

<400> SEQUENCE: 49
ccaatcggac taattcaggt gtgcc                                         25

<210> SEQ ID NO 50
<211> LENGTH: 25
<212> TYPE: DNA
<213> ORGANISM: Homo sapien
<220> FEATURE:
<223> OTHER INFORMATION: 5' primer of Myosin light polypeptide2

<400> SEQUENCE: 50
```
tccaacgtgt tctccatgtt cgaac                                    25

<210> SEQ ID NO 51
<211> LENGTH: 25
<212> TYPE: DNA
<213> ORGANISM: Homo sapien
<220> FEATURE:
<223> OTHER INFORMATION: 3' primer of Myosin light polypeptide2

<400> SEQUENCE: 51
cttgtagtcc aagttgccag tcacg                                    25

<210> SEQ ID NO 52
<211> LENGTH: 26
<212> TYPE: DNA
<213> ORGANISM: Homo sapien
<220> FEATURE:
<223> OTHER INFORMATION: 5' primer of Nerve Growth Factor Receptor

<400> SEQUENCE: 52
tgttctcctg ccaggacaag cagaac                                   26

<210> SEQ ID NO 53
<211> LENGTH: 26
<212> TYPE: DNA
<213> ORGANISM: Homo sapien
<220> FEATURE:
<223> OTHER INFORMATION: 3' primer of Nerve Growth Factor Receptor

<400> SEQUENCE: 53
tcttgaaggc tatgtaggcc acaagg                                   26

<210> SEQ ID NO 54
<211> LENGTH: 24
<212> TYPE: DNA
<213> ORGANISM: Homo sapien
<220> FEATURE:
<223> OTHER INFORMATION: 5' primer of Neurofilament heavy Chain

<400> SEQUENCE: 54
tgaacacaga cgctatgcgc tcag                                     24

<210> SEQ ID NO 55
<211> LENGTH: 25
<212> TYPE: DNA
<213> ORGANISM: Homo sapien
<220> FEATURE:
<223> OTHER INFORMATION: 3' primer of Neurofilament heavy Chain

<400> SEQUENCE: 55
cacctttatg tgagtggaca cagag                                    25

<210> SEQ ID NO 56
<211> LENGTH: 25
<212> TYPE: DNA
<213> ORGANISM: Homo sapien
<220> FEATURE:
<223> OTHER INFORMATION: 5' primer of Octamer Binding Protein 4

<400> SEQUENCE: 56
cgagaagctg gagaaggaga agctg                                    25

<210> SEQ ID NO 57
<211> LENGTH: 25
<212> TYPE: DNA

<213> ORGANISM: Homo sapien
<220> FEATURE:
<223> OTHER INFORMATION: 3' primer of Octamer Binding Protein 4

<400> SEQUENCE: 57
caagggccgc agcttacaca tgttc                                    25

<210> SEQ ID NO 58
<211> LENGTH: 27
<212> TYPE: DNA
<213> ORGANISM: Homo sapien
<220> FEATURE:
<223> OTHER INFORMATION: 5' primer of Parathyroid Hormone

<400> SEQUENCE: 58
ggctaaagtt atgattgtca tgttggc                                  27

<210> SEQ ID NO 59
<211> LENGTH: 25
<212> TYPE: DNA
<213> ORGANISM: Homo sapien
<220> FEATURE:
<223> OTHER INFORMATION: 3' primer of Parathyroid Hormone

<400> SEQUENCE: 59
tcagctttgt ctgcctctcc aagac                                    25

<210> SEQ ID NO 60
<211> LENGTH: 25
<212> TYPE: DNA
<213> ORGANISM: Homo sapien
<220> FEATURE:
<223> OTHER INFORMATION: 5' primer of PDX-1

<400> SEQUENCE: 60
ggatgaagtc taccaaagct cacgc                                    25

<210> SEQ ID NO 61
<211> LENGTH: 25
<212> TYPE: DNA
<213> ORGANISM: Homo sapien
<220> FEATURE:
<223> OTHER INFORMATION: 3' primer of PDX-1

<400> SEQUENCE: 61
ccagatcttg atgtgtctct cggtc                                    25

<210> SEQ ID NO 62
<211> LENGTH: 25
<212> TYPE: DNA
<213> ORGANISM: Homo sapien
<220> FEATURE:
<223> OTHER INFORMATION: 5' primer of Phosphoprotein enriched in
    astrocytes

<400> SEQUENCE: 62
agagtgagga gatcactact ggcag                                    25

<210> SEQ ID NO 63
<211> LENGTH: 25
<212> TYPE: DNA
<213> ORGANISM: Homo sapien
<220> FEATURE:
<223> OTHER INFORMATION: 3' primer of Phosphoprotein enriched in
    astrocytes

<400> SEQUENCE: 63
acctgctggt actcaggaaa cagtc　　　　　　　　　　　　　　　　　　　25

<210> SEQ ID NO 64
<211> LENGTH: 25
<212> TYPE: DNA
<213> ORGANISM: Homo sapien
<220> FEATURE:
<223> OTHER INFORMATION: 5' primer of Renin

<400> SEQUENCE: 64
agtcgtcttt gacactggtt cgtcc　　　　　　　　　　　　　　　　　　　25

<210> SEQ ID NO 65
<211> LENGTH: 24
<212> TYPE: DNA
<213> ORGANISM: Homo sapien
<220> FEATURE:
<223> OTHER INFORMATION: 3' primer of Renin

<400> SEQUENCE: 65
ggtagaacct gagatgtagg atgc　　　　　　　　　　　　　　　　　　　　24

<210> SEQ ID NO 66
<211> LENGTH: 26
<212> TYPE: DNA
<213> ORGANISM: Homo sapien
<220> FEATURE:
<223> OTHER INFORMATION: 5' primer of Retinoic Acid Receptor type alpha

<400> SEQUENCE: 66
agcagcagtt ctgaagagat agtgcc　　　　　　　　　　　　　　　　　　　26

<210> SEQ ID NO 67
<211> LENGTH: 25
<212> TYPE: DNA
<213> ORGANISM: Homo sapien
<220> FEATURE:
<223> OTHER INFORMATION: 3' primer of Retinoic Acid Receptor type alpha

<400> SEQUENCE: 67
gtggagagtt cactgaactt gtccc　　　　　　　　　　　　　　　　　　　25

<210> SEQ ID NO 68
<211> LENGTH: 25
<212> TYPE: DNA
<213> ORGANISM: Homo sapien
<220> FEATURE:
<223> OTHER INFORMATION: 5' primer of Surfactant

<400> SEQUENCE: 68
tccagctcat ctagatgagg agctc　　　　　　　　　　　　　　　　　　　25

<210> SEQ ID NO 69
<211> LENGTH: 25
<212> TYPE: DNA
<213> ORGANISM: Homo sapien
<220> FEATURE:
<223> OTHER INFORMATION: 3' primer of Surfactant

<400> SEQUENCE: 69
gtcccatggc ctaaatgcct ctcag　　　　　　　　　　　　　　　　　　　25

<210> SEQ ID NO 70
<211> LENGTH: 26
<212> TYPE: DNA

```
<213> ORGANISM: Homo sapien
<220> FEATURE:
<223> OTHER INFORMATION: 5' primer of Transforming Growth Factor
      Receptor type

<400> SEQUENCE: 70
tagtcactga caacaacggt gcagtc                                              26

<210> SEQ ID NO 71
<211> LENGTH: 25
<212> TYPE: DNA
<213> ORGANISM: Homo sapien
<220> FEATURE:
<223> OTHER INFORMATION: 3' ' primer of Surfactant

<400> SEQUENCE: 71
acagtgctcg ctgaactcca tgagc                                               25

<210> SEQ ID NO 72
<211> LENGTH: 24
<212> TYPE: DNA
<213> ORGANISM: Homo sapien
<220> FEATURE:
<223> OTHER INFORMATION: 5' primer of WT 1

<400> SEQUENCE: 72
tccttcatca aacaggagcc gagc                                                24

<210> SEQ ID NO 73
<211> LENGTH: 25
<212> TYPE: DNA
<213> ORGANISM: Homo sapien
<220> FEATURE:
<223> OTHER INFORMATION: 3' primer of WT 1

<400> SEQUENCE: 73
ctgtagggcg tcctcagcag caaag                                               25
```